US012797090B2

(12) United States Patent
Estay et al.

(10) Patent No.: US 12,797,090 B2
(45) Date of Patent: Nov. 17, 2026

(54) SYSTEMS AND METHODS FOR AN ULTRASOUND CATHETER

(71) Applicant: SonoVascular, Inc., Chapel Hill, NC (US)

(72) Inventors: Daniel Enrique Estay, Chapel Hill, NC (US); Leslie Segal Purcell, Chapel Hill, NC (US); Bradley James Stringer, Ridgefield, WA (US); John William Ranshaw, Charlotte, NC (US)

(73) Assignee: Sonovascular, Inc., Chapel Hills (NC)

( * ) Notice: Subject to any disclaimer, the term of this patent is extended or adjusted under 35 U.S.C. 154(b) by 0 days.

(21) Appl. No.: 19/108,606

(22) PCT Filed: Sep. 8, 2023

(86) PCT No.: PCT/US2023/032316
§ 371 (c)(1),
(2) Date: Mar. 4, 2025

(87) PCT Pub. No.: WO2024/054648
PCT Pub. Date: Mar. 14, 2024

(65) Prior Publication Data

US 2026/0076695 A1 Mar. 19, 2026

Related U.S. Application Data

(60) Provisional application No. 63/375,038, filed on Sep. 8, 2022.

(51) Int. Cl.
*A61B 17/22* (2006.01)
*A61B 17/00* (2006.01)

(52) U.S. Cl.
CPC .... *A61B 17/22012* (2013.01); *A61B 17/2202* (2013.01); *A61B 17/22031* (2013.01);
(Continued)

(58) Field of Classification Search
CPC .......... A61B 17/22012; A61B 17/2202; A61B 17/22031; A61B 2017/00778;
(Continued)

(56) References Cited

U.S. PATENT DOCUMENTS 4,276,885 A 7/1981 Tickner et al.
4,375,818 A 3/1983 Suwaki et al.
(Continued)

FOREIGN PATENT DOCUMENTS

CN 102232857 11/2011
CN 205548629 9/2016
(Continued)

OTHER PUBLICATIONS

International Search Report and Written Opinion issued in PCT Application No. PCT/US2023/032316, mailed Jan. 9, 2024, in 19 pages.
(Continued)

*Primary Examiner* — Dung T Ulsh
(74) *Attorney, Agent, or Firm* — Knobbe Martens Olson & Bear, LLP

(57) ABSTRACT

A catheter system includes an aspiration catheter (300) having a first end, a second end, and a body positioned between the first end and the second end. An ultrasound catheter (200) having a proximal end, a distal end, and a body positioned between the proximal end and the distal end. The ultrasound catheter (200) is configured to be inserted through the body of the aspiration catheter (300). The distal end of the ultrasound catheter is configured to articulate. A retriever catheter (400) has a proximal end, a distal end, and a shaft positioned between the proximal end and the distal end. The retriever catheter (400) configured to inserted through the body of the aspiration catheter.

20 Claims, 13 Drawing Sheets

(52) U.S. Cl.
CPC ............... *A61B 2017/00778* (2013.01); *A61B 2017/22007* (2013.01); *A61B 2017/22035* (2013.01); *A61B 2217/005* (2013.01)

(58) Field of Classification Search
CPC ........... A61B 2017/22007; A61B 2017/22035; A61B 2217/005
See application file for complete search history.

(56) References Cited

U.S. PATENT DOCUMENTS 4,808,153 A 2/1989 Parisi
4,927,427 A 5/1990 Kriauciunas et al.
4,951,677 A 8/1990 Crowley et al.
5,011,488 A 4/1991 Ginsburg et al.
5,099,693 A 3/1992 Payne et al.
5,329,496 A 7/1994 Smith
5,377,682 A 1/1995 Ueno et al.
5,413,550 A 5/1995 Castel
5,454,373 A 10/1995 Koger et al.
5,558,092 A 9/1996 Unger et al.
5,581,144 A 12/1996 Corl et al.
5,695,460 A 12/1997 Siegel et al.
5,718,231 A 2/1998 Dewhurst et al.
6,022,309 A 2/2000 Celliers et al.
6,197,345 B1 3/2001 Porter
6,221,006 B1 4/2001 Dubrul et al.
6,312,444 B1 11/2001 Barbut et al.
6,413,216 B1 7/2002 Cain et al.
6,464,680 B1 10/2002 Brisken
6,478,765 B2 11/2002 Siegel et al.
6,484,052 B1 11/2002 Visuri et al.
6,585,678 B1 7/2003 Tachibana et al.
6,656,124 B2 12/2003 Flesch et al.
6,695,858 B1 2/2004 Dubrul et al.
6,896,659 B2 5/2005 Conston et al.
6,942,677 B2 9/2005 Nita et al.
6,979,293 B2 12/2005 Hansmann et al.
7,341,569 B2 3/2008 Soltani et al.
7,491,210 B2 2/2009 Dubrul et al.
7,622,853 B2 11/2009 Rehrig et al.
7,648,478 B2 1/2010 Soltani et al.
7,686,825 B2 * 3/2010 Hauser .................. A61F 2/0105
606/200
7,771,372 B2 8/2010 Wilson
7,905,836 B2 3/2011 Dan
7,955,293 B2 6/2011 Nita et al.
8,066,757 B2 11/2011 Ferrera et al.
8,148,877 B2 4/2012 Jiang et al.
8,252,020 B2 8/2012 Hauser et al.
8,328,820 B2 12/2012 Diamant et al.
8,364,256 B2 1/2013 Leuer et al.
8,613,751 B2 12/2013 Nita et al.
8,622,911 B2 1/2014 Hossack et al.
8,668,709 B2 3/2014 Nita et al.
8,740,835 B2 6/2014 Soltani et al.
8,795,345 B2 8/2014 Grandfield et al.
8,801,748 B2 8/2014 Martin
8,926,630 B2 1/2015 Diamant et al.
8,956,386 B2 2/2015 Hauser et al.
9,017,309 B2 4/2015 Tanikawa et al.
9,067,053 B2 6/2015 Asami et al.
9,192,566 B2 11/2015 Soltani et al.
9,237,898 B2 1/2016 Hossack et al.
9,387,098 B2 7/2016 Ferrera et al.
9,526,922 B2 12/2016 Hossack et al.
9,675,820 B2 6/2017 Holland et al.
9,700,283 B2 7/2017 Garbini
9,844,387 B2 12/2017 Marchand et al.
9,848,975 B2 12/2017 Hauser
9,895,158 B2 2/2018 Dixon et al.
9,924,958 B2 3/2018 Martin et al.
9,955,946 B2 5/2018 Miller et al.
10,016,266 B2 7/2018 Hauser
10,064,635 B2 9/2018 Martin et al.
10,076,347 B2 9/2018 Sepetka et al.
10,219,815 B2 3/2019 Maxwell et al.
10,328,290 B2 6/2019 Zhou et al.
10,350,386 B2 7/2019 di Palma et al.
10,383,644 B2 8/2019 Molaei et al.
10,413,278 B2 9/2019 Chen et al.
10,492,805 B2 12/2019 Culbert et al.
10,492,855 B2 12/2019 Katoh et al.
10,507,315 B2 12/2019 Hossack et al.
10,639,051 B2 5/2020 Cioanta et al.
10,682,152 B2 6/2020 Vale et al.
10,687,832 B2 6/2020 Stigall et al.
10,695,159 B2 6/2020 Hauser
10,799,331 B2 10/2020 Hauser
10,835,271 B2 11/2020 Ma
10,893,881 B2 1/2021 Dixon et al.
11,000,672 B2 5/2021 Walzman
11,013,523 B2 5/2021 Hadar
11,051,833 B2 7/2021 Martin
11,058,901 B2 7/2021 Soltani et al.
11,083,473 B2 8/2021 Sudin et al.
11,123,089 B2 9/2021 Ma
11,147,572 B2 10/2021 Vale et al.
11,166,738 B2 11/2021 Gogoussis et al.
11,202,646 B2 12/2021 Martin et al.
11,273,329 B2 3/2022 Konofagou et al.
11,291,463 B2 4/2022 Atchaneeyasakul et al.
11,419,620 B2 8/2022 Cooper et al.
11,529,157 B2 12/2022 Brady et al.
11,529,158 B2 12/2022 Hauser
11,534,188 B2 12/2022 Imai et al.
11,589,885 B2 2/2023 Gamba et al.
11,793,541 B2 10/2023 Shen
11,806,033 B2 11/2023 Marchand et al.
11,812,981 B2 11/2023 Lorenzo et al.
11,832,837 B2 12/2023 Hauser
11,832,838 B2 12/2023 Hauser
11,839,393 B2 12/2023 Hauser
11,883,679 B2 1/2024 Jiang et al.
11,925,369 B2 3/2024 Hauser
11,969,178 B2 4/2024 Hauser
12,023,057 B2 7/2024 Hauser
12,064,650 B2 8/2024 Soltani et al.
12,186,595 B2 1/2025 Soltani et al.
12,458,379 B2 11/2025 Allen
2002/0009391 A1 1/2002 Marquiss et al.
2002/0043896 A1 4/2002 Hashimoto
2003/0078227 A1 4/2003 Greenleaf et al.
2004/0251784 A1 12/2004 Kuniyasu
2005/0192556 A1 9/2005 Soltani et al.
2005/0245891 A1 11/2005 McCormick et al.
2006/0155305 A1 7/2006 Freudenthal et al.
2006/0264809 A1 11/2006 Hansmann et al.
2008/0200845 A1 8/2008 Sokka et al.
2009/0108710 A1 4/2009 Brown et al.
2009/0131798 A1 5/2009 Minar et al.
2009/0221902 A1 9/2009 Myhr
2009/0222035 A1 9/2009 Cooper et al.
2010/0089133 A1 4/2010 Yamasaki et al.
2010/0160779 A1 6/2010 Browning et al.
2011/0288449 A1 11/2011 Schenkengel
2012/0209116 A1 8/2012 Hossack et al.
2012/0259314 A1 10/2012 Guo et al.
2013/0150725 A1 6/2013 Choi
2013/0289608 A1 10/2013 Tanaka et al.
2014/0039358 A1 2/2014 Zhou et al.
2014/0112107 A1 4/2014 Guo et al.
2014/0142468 A1 5/2014 Hossack et al.
2014/0180128 A1 6/2014 Corl
2015/0141833 A1 5/2015 Dayton et al.
2015/0265299 A1 9/2015 Schneiderman
2016/0262727 A1 9/2016 Dayton et al.
2016/0367839 A1 12/2016 Hoelscher et al.
2016/0374710 A1 12/2016 Sinelnikov et al.
2018/0206867 A1 7/2018 Allen
2018/0280005 A1 * 10/2018 Parmentier .......... A61B 17/221
2019/0216478 A1 7/2019 Maxwell et al.
2019/0223895 A1 7/2019 Volz
2019/0262594 A1 8/2019 Ogata et al.

(56) References Cited

U.S. PATENT DOCUMENTS

| | | | |
|---|---|---|---|
| 2019/0388109 | A1 | 12/2019 | Cai et al. |
| 2020/0055013 | A1 | 2/2020 | Son et al. |
| 2020/0107843 | A1 | 4/2020 | Goertz et al. |
| 2020/0281612 | A1 | 9/2020 | Kelly et al. |
| 2020/0297364 | A1 | 9/2020 | Choe et al. |
| 2020/0338172 | A1 | 10/2020 | Pacella et al. |
| 2020/0397452 | A1 | 12/2020 | Twomet et al. |
| 2020/0405258 | A1 | 12/2020 | Dayton et al. |
| 2021/0007759 | A1 | 1/2021 | Jiang et al. |
| 2021/0022843 | A1 | 1/2021 | Hauser |
| 2021/0153883 | A1 | 5/2021 | Casey |
| 2021/0154433 | A1 | 5/2021 | Casey et al. |
| 2021/0187244 | A1 | 6/2021 | Buck et al. |
| 2021/0228224 | A1 | 7/2021 | Razack |
| 2021/0236150 | A1 | 8/2021 | Hadar |
| 2021/0236257 | A1 | 8/2021 | Walzman |
| 2021/0267614 | A1 | 9/2021 | Jiang et al. |
| 2021/0298773 | A1 | 9/2021 | Echarri et al. |
| 2021/0339055 | A1 | 11/2021 | Soltani et al. |
| 2021/0378694 | A1 | 12/2021 | Thress et al. |
| 2022/0000500 | A1 | 1/2022 | Hadar et al. |
| 2022/0000506 | A1 | 1/2022 | Hauser |
| 2022/0000508 | A1 | 1/2022 | Schmitt et al. |
| 2022/0061869 | A1 | 3/2022 | Fermi et al. |
| 2022/0071705 | A1 | 3/2022 | Yang et al. |
| 2022/0117614 | A1 | 4/2022 | Salmon et al. |
| 2022/0125453 | A1 | 4/2022 | Nguyen |
| 2022/0160383 | A1 | 5/2022 | Hauser |
| 2022/0175411 | A1 | 6/2022 | Park et al. |
| 2022/0240955 | A1 | 8/2022 | Walzman |
| 2022/0296215 | A1 | 9/2022 | Guo et al. |
| 2022/0378446 | A1 | 12/2022 | Culbert et al. |
| 2022/0378448 | A1 | 12/2022 | Culbert et al. |
| 2022/0395284 | A1 | 12/2022 | Cooper et al. |
| 2023/0051315 | A1 | 2/2023 | Loftman et al. |
| 2023/0127145 | A1 | 4/2023 | Hadar et al. |
| 2023/0133123 | A1 | 5/2023 | Walzman |
| 2023/0165559 | A1 | 6/2023 | Sutherland et al. |
| 2023/0233800 | A1 | 7/2023 | Howell et al. |
| 2025/0017608 | A1 | 1/2025 | Dayton et al. |
| 2025/0058627 | A1 | 2/2025 | Miller et al. |
| 2025/0064469 | A1 | 2/2025 | Jiang et al. |
| 2025/0128098 | A1 | 4/2025 | Soltani et al. |
| 2025/0228576 | A1 | 7/2025 | Jiang et al. |
| 2025/0288307 | A1 | 9/2025 | Jiang et al. |
| 2026/0033848 | A1 | 2/2026 | Jiang et al. |
| 2026/0207211 | A1 | 7/2026 | Stringer et al. |

FOREIGN PATENT DOCUMENTS

| | | |
|---|---|---|
| CN | 109480958 | 3/2019 |
| CN | 110522992 | 12/2019 |
| CN | 111905236 | 11/2020 |
| CN | 113598885 | 11/2021 |
| CN | 113974765 | 1/2022 |
| CN | 114041849 | 2/2022 |
| CN | 114191154 | 3/2022 |
| CN | 114376672 | 4/2022 |
| CN | 115486899 | 11/2024 |
| DE | 10146011 | 4/2003 |
| EP | 0576607 | 1/1994 |
| EP | 1701750 | 8/2013 |
| EP | 2319575 | 11/2013 |
| EP | 2979649 | 2/2016 |
| EP | 1553996 | 3/2017 |
| EP | 1594424 | 10/2018 |
| EP | 2456369 | 10/2018 |
| EP | 3346925 | 5/2019 |
| EP | 2214573 | 7/2019 |
| EP | 3539486 | 9/2019 |
| EP | 3801307 | 4/2021 |
| EP | 2958616 | 1/2024 |
| EP | 3880090 | 7/2024 |
| EP | 3244813 | 11/2024 |
| KR | 102125615 | 6/2020 |
| WO | WO 2005/112770 | 12/2005 |
| WO | WO 2012/011097 | 1/2012 |
| WO | WO 2012/162664 | 11/2012 |
| WO | WO 2013/053099 | 4/2013 |
| WO | WO 2013/181194 | 12/2013 |
| WO | WO 2021/239878 | 12/2021 |
| WO | WO 2021/247544 | 12/2021 |
| WO | WO 2022/123565 | 6/2022 |
| WO | WO 2023/087475 | 5/2023 |
| WO | WO 2023/102104 | 6/2023 |
| WO | WO 2024/054648 | 3/2024 |
| WO | WO 2025/128583 | 6/2025 |
| WO | WO 2025/193839 | 9/2025 |

OTHER PUBLICATIONS

Acconcia et al., "Interactions Between Individual Ultrasound-Stimulated Microbubbles and Fibrin Clots," Ultrasound in Med. & Biol., vol. 40, No. 9, pp. 1-17 (2014).

Acconcia et al., "The Effect of Short Duration Ultrasound Pulses on the Interaction Between Individual Microbubbles and Fibrin Clots," Ultrasound in Med. & Biol., vol. 41, No. 10, pp. 1-9 (2015).

Alfonso et al., "Current Treatment of In-Stent Restenosis," Journal of the American College of Cardiology, vol. 63, No. 24, pp. 2659-2673, 2014.

Anderson et al., "A Population-Based Perspective of the Hospital Incidence and Case-Fatality Rates of Deep Vein Thrombosis and Pulmonary Embolism," Arch Intern Med, vol. 151, pp. 1-6 (May 1991).

Aoki et al., Optimal Approach for Treating In-Stent Restenosis, Cardiac Interventions Today, 2018.

Bader et al., "Efficacy of histotripsy combined with rt-PA in vitro," Phys Med Biol., vol. 61, No. 14, pp. 1-35 (Jul. 21, 2016).

Ballehaninna et al., "Acute superior mesenteric artery embolism: reperfusion with AngioJet hydrodynamic suction thrombectomy and pharmacologic thrombolysis with the EKOS catheter," Vascular, vol. 20, No. 3, pp. 166-170 (2012).

Beckman et al., "Venous Thromboembolism A Public Health Concern," Am J Prev Med, vol. 38, No. 4S, pp. 1-7 (2010).

Behler et al., T. C. Nichols, H. Zhu, E. P. Merricks, and C. M. Gallippi, "ARFI imaging for noninvasive material characterization of atherosclerosis. Part II: toward in vivo characterization," Ultrasound in Medicine & Biology, vol. 35, No. 2, pp. 278-295, 2009.

Benjamin et al. "Heart disease and stroke statistics—2019 update: a report from the American heart association," Circulation, vol. 139, No. 10, pp. e56-e528, 2019.

Bilen et al., L. T. Sener, I. Albeniz, M. Sezen, M. B. Unlu, and M. Ugurlucan, "Determination of ultrastructural properties of human carotid atherosclerotic plaques by scanning acoustic microscopy, micro-computer tomography, scanning electron microscopy and energy dispersive X-ray spectroscopy," Scientific Reports, vol. 9, No. 1, pp. 1-10, 2019.

Brace, "Thermal Tumor Ablation in Clinical Use," IEEE Pulse, vol. 2, No. 5, pp. 28-38, 2011.

Briguori et al., "In-stent restenosis in small coronary arteries: impact of strut thickness," Journal of the American College of Cardiology, vol. 40, No. 3, pp. 403-409, 2002.

Brubler et al., "Nanoscaled ultrasound contrast agents for enhanced sonothrombolysis," Colloids and Surfaces B: Biointerfaces, vol. 172, pp. 1-6 (2018).

Buccheri et al., "Understanding and managing in-stent restenosis: a review of clinical data, from pathogenesis to treatment," Journal of Thoracic Disease, vol. 8, No. 10, pp. E1150-E1162, 2016.

Burgess et al., "High-Intensity Focused Ultrasound (HIFU) for Dissolution of Clots in a Rabbit Model of Embolic Stroke," PLoS One, vol. 7, No. 8, pp. 1-7 (Aug. 2012).

Canney et al., A multi element interstitial ultrasound applicator for the thermal therapy of brain tumors. The Journal of the Acoustical Society of America, vol. 134, No. 2, pp. 1647-1655, 2013.

Cao et al., "High-sensitivity intravascular photoacoustic imaging of lipid-laden plaque with a collinear catheter design," Scientific Reports, vol. 6, No. 1, 2016.

(56) References Cited

OTHER PUBLICATIONS

Cassese et al., "Incidence and predictors of restenosis after coronary stenting in 10,004 patients with surveillance angiography," Heart, vol. 100, No. 2, pp. 153-159, (2013).
Chaussy et al., "High-intensity focused ultrasound for the treatment of prostate cancer: a review," Journal of Endourology, vol. 31, No. S1, pp. S30-37, 2017.
Cheng et al., "Factors influencing stent restenosis after percutaneous coronary intervention in patients with coronary heart disease: a clinical trial based on 1-year follow-up," Medical Science Monitor: International Medical Journal of Experimental and Clinical Research, vol. 25, pp. 240-247, 2019.
Chopra et al., "MRI compatible transurethral ultrasound system for the treatment of localized prostate cancer using rotational control," Medical physics, vol. 35, No. 4, pp. 1346-1357, 2008.
Chu et al., "Focused Ultrasound-Induced Blood-Brain Barrier Opening: Association with Mechanical Index and Cavitation Index Analyzed by Dynamic Contrast-Enhanced Magnetic-Resonance Imaging," Nature, Scientific Reports, vol. 6, No. 33264, pp. 1-13 (Sep. 15, 2016).
Cosgrave et al., "Repeated drug-eluting stent implantation for drug-eluting stent restenosis: the same or a different stent," American Heart Journal, vol. 153, No. 3, pp. 354-359, 2007.
Czernuszewicz et al., "Non-invasive in vivo characterization of human carotid plaques with acoustic radiation force impulse ultrasound: comparison with histology after endarterectomy," Ultrasound in medicine & biology, vol. 41, No. 3, pp. 685-697, 2015.
Czernuszewicz et al., "Performance of acoustic radiation force impulse ultrasound imaging for carotid plaque characterization with histologic validation," Journal of Vascular Surgery, vol. 66, No. 6, pp. 1749-1757, 2017.
Datta et al., "Correlation of Cavitation with Ultrasound Enhancement of Thrombolysis," Ultrasound Med Biol., vol. 32, No. 8, pp. 1-20 (Aug. 2006).
Datta et al., "Ultrasound-enhanced thrombolysis using Definity as a cavitation nucleation agent," Ultrasound Med Biol., vol. 34, No. 9, pp. 1-24 (Sep. 2008).
Dauerman et al., "Mechanical debulking versus balloon angioplasty for the treatment of true bifurcation lesions," Journal of the American College of Cardiology, vol. 32, No. 7, pp. 1845-1852, 1998.
Davis et al., "Targeted disruption of LDLR causes hypercholesterolemia and atherosclerosis in Yucatan miniature pigs," PLoS One, vol. 9, No. 4, e93457, 2014.
Deora et al., "Bioresorbable Vascular Scaffold for Coronary In-Stent Restenosis: a Novel Concept," Indian Heart Journal, vol. 66, No. 4, pp. 459-461, 2014.
DiNisio et al., "Deep vein thrombosis and pulmonary embolism," Lancet, vol. 388, pp. 1-14 (Jun. 30, 2016).
Dixon et al., "Enhanced Intracellular Delivery of a Model Drug Using Microbubbles Produced by a Microfluidic Device," Ultrasound in Med. & Biol., vol. 39, No. 7, pp. 1-10 (2013).
Dixon et al., "Microbubble-Mediated Intravascular Ultrasound Imaging and Drug Delivery," IEEE Transactions on Ultrasonics, Ferroelectrics, and Frequency Control, vol. 62, No. 9, pp. 1-12 (Sep. 2015).
Engelberger et al., "Enhanced Thrombolysis by Ultrasound-Assisted Catheter-Directed Thrombolysis and Microbubbles in an In Vitro Model of Iliofemoral Deep Vein Thrombosis," Thrombosis and Haemostasis, vol. 119, No. Jul. 2019, pp. 1094-1101 (Jun. 5, 2019).
Engelberger et al., Ultrasound-Assisted Versus Conventional Catheter-Directed Thrombolysis for Acute Iliofemoral Deep Vein Thrombosis, Circ Cardiovasc Interv, pp. 1-9 (2015).
Escoffre et al., "Therapeutic Ultrasound," Advances in Experimental Medicine and Biology, vol. 880, pp. 1-15 (2016).
Fan et al., "Nonlinear Constitutive Behavior of Soft and Hard PZT: Experiments and Modeling," Acta mater., vol. 47, No. 17, pp. 4415-4425 (1999).
Fix et al., "An evaluation of the sonoporation potential of low-boiling point phase-change ultrasound contrast agents in vitro," Journal of Therapeutic Ultrasound, vol. 5, No. 7, pp. 1-11 (2017).
Foin et al., "Incomplete stent apposition causes high shear flow disturbances and delay in neointimal coverage as a function of strut to wall detachment distance: implications for the management of incomplete stent apposition," Circulation: Cardiovascular Interventions, vol. 7, No. 2, pp. 180-189, 2014.
Galanaud et al., "The history and historical treatments of deep vein thrombosis," Journal of Thrombosis and Haemostasis, vol. 11, pp. 1-10 (2013).
Galiuto et al., "The EAE Textbook of Echocardiography," European Society of Cardiology, 2 ed., pp. 1-37 (May 2011).
Giacoppo et al., "Treatment strategies for coronary in-stent restenosis: systematic review and hierarchical bayesian network meta-analysis of 24 randomised trials and 4880 patients," BMJ, vol. 351, h5392, 2015.
Goel et al., "Advances in Sonothrombolysis Techniques Using Piezoelectric Transducers," Sensors, vol. 20, pp. 1-17 (2020).
Goel et al., "Examining the Influence of Low-Dose Tissue Plasminogen Activator on Microbubble-Mediated Forward-Viewing Intravascular Sonothrombolysis," Ultrasound in Med. & Biol., vol. 46, No. 7, pp. 1-9 (2020).
Goel et al., "Intravascular Sonothrombolysis, In Vitro, Using a Small Aperture, Forward-Viewing, Sub-Megahertz Transducer to Enhance tPA Treatment," IEEE International Ultrasonics Symposium (IUS), pp. 2034-2036, 2019.
Goodman, "Toward Evidence-Based Medical Statistics. 1: The P Value Fallacy," Ann Intern Med., pp. 995-1004 (1999).
Goudot et al., "Pulsed cavitational therapy using high-frequency ultrasound for the treatment of deep vein thrombosis in an in vitro model of human blood clot," Physics in Medicine and Biology, vol. 62, No. 24, pp. 1-26 (2017).
Greenfield et al., "Recurrent thromboembolism in patients with vena cava filters," Journal of Vascular Surgery, vol. 33, No. 3, pp. 510-514 (2001).
Grunwald et al., "Identification of a novel Arg→ Cys mutation in the LDL receptor that contributes to spontaneous hypercholesterolemia in pigs. Journal of lipid research," vol. 40, No. 3, pp. 475-485, 1999.
Guo et al., "Reduced clot debris size in sonothrombolysis assisted with phase-change nanodroplets," Ultrasonics—Sonochemistry, vol. 54, pp. 1-9 (2019).
Hanet et al., "Influence of balloon size and stenosis morphology on immediate and delayed elastic recoil after percutaneous transluminal coronary angioplasty," Journal of the American College of Cardiology, vol. 18, No. 2, pp. 506-511, 1991.
Hasler-Rapacz et al., "Identification of a mutation in the low density lipoprotein receptor gene associated with recessive familial hypercholesterolemia in swine," American Journal of Medical Genetics, vol. 76, No. 5, pp. 379-386, 1998.
Heit, "Epidemiology of venous thromboembolism," Nat Rev Cardiol., vol. 12, No. 8, pp. 1-27 (Aug. 2015).
Her et al., "Current Management of In-Stent Restenosis," Korean Circulation Journal, vol. 48, No. 5, pp. 337-349, 2018.
Hill et al., "High intensity focused ultrasound-potential for cancer treatment," The British Journal of Radiology, vol. 68, No. 816, pp. 1296-1303, 1995.
Hoffmann et al., "Patterns and mechanisms of in-stent restenosis: a serial intravascular ultrasound study," Circulation, vol. 94, No. 6, pp. 1247-1254, 1996.
Holscher et al., "Effects of varying duty cycle and pulse width on high-intensity focused ultrasound (HIFU)-induced transcranial thrombolysis," Journal of Therapeutic Ultrasound, vol. 1, No. 18, pp. 1-5 (2013).
Holscher et al., "Noninvasive Transcranial Clot Lysis Using High Intensity Focused Ultrasound," J Neurol Neurophysiol, pp. 1-7 (2011).
Illing et al., "The safety and feasibility of extracorpoeal high-intensity focused ultrasound (HIFU) for the treatment of liver and kidney tumours in a western population," British Journal of Cancer, vol. 93, No. 8, pp. 890-895, 2005.

(56) References Cited

OTHER PUBLICATIONS

Iserson, "J.-F.-B. Charriere: the man behind the "French" gauge," The Journal of emergency medicine, vol. 5, No. 6, pp. 545-548, 1987.
Jin et al., "Ultrasound-triggered thrombolysis using urokinase-loaded nanogels," International Journal of Pharmaceutics, vol. 434, pp. 1-7 (2012).
Johnston et al., "Mechanical characterization of bulk Sylgard 184 for microfluidics and microengineering," J. Micromech. Microeng., vol. 24, pp. 1-9 (2014).
Kahn, "The Clinical Diagnosis of Deep Venous Thrombosis," Arch Intern Med., vol. 158, pp. 1-9 (Nov. 23, 1998).
Karthikesalingam et al., "A Systematic Review of Percutaneous Mechanical Thrombectomy in the Treatment of Deep Venous Thrombosis," Eur J Vasc Endovasc Surg, vol. 41, pp. 1-12 (2011).
Kastrati et al., "Predictive factors of restenosis after coronary stent placement. Journal of the American College of Cardiology," vol. 30, No. 6, pp. 1428-1436, 1997.
Khokhlova et al., "Histotripsy methods in mechanical disintegration of tissue: towards clinical applications," International Journal of Hyperthermia, vol. 31, No. 2, pp. 145-162, 2015.
Kim et al., "Intravascular forward-looking ultrasound transducers for microbubble-mediated sonothrombolysis", Scientific Reports 7.1, (2017); 1-10.
Kim et al., "Miniaturized Focused Ultrasound Transducers for Intravascular Therapies", ASME, Nov. 3-9, 2017.
Kim et al., "A Comparison of Sonothrombolysis in Aged Clots Between Low-Boiling-Point Phase-Change Nanodroplets and Microbubbles of the Same Composition," Ultrasound in Med. & Biol., vol. 46, No. 11, pp. 1-10 (2020).
Kim et al., "Homogenization of PMN-PT/epoxy 1-3 piezocomposites by resonator measurements and finite element analysis ," Sensors and Actuators A, vol. 206, pp. 1-10 (2014).
Kim et al., "Miniaturized Intracavitary Forward-Looking Ultrasound Transducer for Tissue Ablation," IEEE Transactions on Biomedical Engineering, vol. 67, No. 7, pp. 1-10 (Jul. 2020).
Kim et al., "Phantom evaluation of stacked-type dual-frequency 1-3 composite transducers: A feasibility study on intracavitary acoustic angiography," Ultrasonics, vol. 63, pp. 1-9 (2015).
Kim et al., "Small Aperture Ultrasound Transducers for Intracavitary Tissue Ablation," IEEE International Ultrasonics Symposium (IUS), pp. 1842-1845, 2019.
Kim et al., "Miniaturized Ultrasound Transducer Composed of a Composite of Multiple Piezoelectric Stacks," ASME International Mechanical Engineering Congress and Exposition, 2019.
Kim et al., "Laser-Generated-focused Ultrasound Transducers for Microbubble-Mediated, Dual-Excitation Sonothrombolysis," IEEE International Ultrasonics Symposium (IUS), 2016.
Kukizaki, et al., "Effect of surfactant type on microbubble formation behavior using Shirasu porous glass (SPG) membranes", Colloids and Surfaces A: Physiochemical and Engineering Aspects 326, p. 129-137. (Year:2008).
Kuo et al., "Catheter-directed Therapy for the Treatment of Massive Pulmonary Embolism: Systematic Review and Meta-analysis of Modern Techniques," J Vasc Interv Radiol, vol. 20, pp. 1-10 (2009).
Li et al., "Development of Piezoelectric Ultrasonic Thrombolysis Device for Blood Clot Emulsification," International Scholarly Research Network, vol. 2012, pp. 1-7 (2012).
Li et al., "Quantifying Activation of Perfluorocarbon-Based Phase-Change Contrast Agents UsingSimultaneous Acoustic and Optical Observation," Ultrasound Med Biol., vol. 41, No. 5, pp. 1-20 (May 2015).
Li et al., "Spontaneous Nucleation of Stable Perfluorocarbon Emulsions for Ultrasound Contrast Agents," Nano Lett., vol. 19, pp. 1-9 (2019).
Lindsey et al., "On the relationship between microbubble fragmentation, deflation, and broadband superharmonic signal production," Ultrasound Med Biol., vol. 41, No. 6, pp. 1-30 (Jun. 2015).
Litvack et al., "Role of laser and thermal ablation devices in the treatment of vascular diseases," The American Journal of Cardiology, vol. 61, No. 14, pp. 81G-86G, 1988.
Liu et al., "High-resolution intravascular MRI-guided perivascular ultrasound ablation," Magn Reson Med., vol. 83, pp. 1-14 (2020).
Luke et al., "Super-Resolution Ultrasound Imaging in Vivo with Transient Laser-Activated Nanodroplets," Nano Lett., vol. 16, No. 4, pp. 1-9 (Apr. 13, 2016).
Ma et al., "Deep Penetration of Targeted Nanobubbles Enhanced Cavitation Effect on Thrombolytic Capacity," Bioconjugate Chem, vol. 31, pp. 1-6 (2020).
Ma et al., "Design, Fabrication, and Characterization of a Single-Aperture 1.5-MHz/3-MHz Dual-Frequency HIFU Transducer," IEEE Transactions of Ultrasonics, Ferroelectrics, and Frequency Control, vol. 60, No. 7, pp. 1-12 (Jul. 2013).
Machino-Ohtsuka et al., "Combined assessment of carotid vulnerable plaque, renal insufficiency, eosinophilia, and hs-CRP for predicting risky aortic plaque of cholesterol crystal embolism," Circulation Journal, vol. 74, No. 1, pp. 51-58, 2010.
Maile et al., "A monoclonal antibody against aVB3 integrin inhibits development of atherosclerotic lesions in diabetic pigs. Science translational medicine," vol. 2, No. 18, 18ra11, 2010.
Maile et al., "An anti-aVB3 antibody inhibits coronary artery atherosclerosis in diabetic pigs," Atherosclerosis, vol. 258, pp. 40-50, 2017.
Mast et al., "Treatment of rabbit liver cancer in vivo using miniaturized image-ablate ultrasound arrays," Ultrasound in Medicine and Biology, vol. 37, No. 10, pp. 1609-1621, 2011.
Maxwell et al., "Cavitation clouds created by shock scattering from bubbles during histotripsy," J. Acoust. Soc. Am., vol. 130, No. 4, pp. 1888-1898 (Oct. 2011).
Mazzolai et al., "Diagnosis and management of acute deep vein thrombosis: a joint consensus document from the European Society of Cardiology working groups of aorta and peripheral vascular diseases and pulmonary circulation and right ventricular function," European Heart Journal, vol. 39, pp. 1-14 (2018).
Mehran et al., "Treatment of in-stent restenosis with excimer laser coronary angioplasty versus rotational atherectomy: comparative mechanisms and results," Circulation, vol. 101, No. 21, pp. 2484-2489, 2000.
Melodelima et al., "Transoesophageal Ultrasound Applicator for Sector-Based Thermal Ablation: First In Vivo Experiments," Ultrasound in Med. & Biol., vol. 29, No. 2, pp. 1-7 (2003).
Mills et al., "Multi-Layered PZT/Polymer Composites to Increase Signal-to-Noise Ratio and Resolution for Medical Ultrasound Transducers Part II: Thick Film Technology," IEEE Transactions on Ultrasonics, Ferroelectrics, and Frequency Control, vol. 49, No. 7, pp. 1005-1014 (Jul. 2002).
Mitragotri, "Healing sound: the use of ultrasound in drug delivery and other therapeutic applications," Drug Discovery, vol. 4, pp. 1-6 (Mar. 2005).
Moyer et al., "High-intensity focused ultrasound ablation enhancement in vivo via phase-shift nanodroplets compared to microbubbles," Journal of Therapeutic Ultrasound, vol. 3, No. 7, pp. 1-9 (2015).
Muramatsu et al., "Efficacy of Cutting Balloon Angioplasty for In-Stent Restenosis: an Intravascular Ultrasound Evaluation," The Journal of Invasive Cardiology, vol. 13, No. 6, pp. 439-444, 2001.
Nakatani et al., "Mechanisms of restenosis after coronary intervention: difference between plain old balloon angioplasty and stenting," Cardiovascular Pathology, vol. 12, No. 1, pp. 40-48, 2003.
Nakazawa et al., "The pathology of neoatherosclerosis in human coronary implants: bare-metal and drug-eluting stents," Journal of the American College of Cardiology, vol. 57, No. 11, pp. 1314-1322, 2011.
Nichols et al., "Oxidized LDL and fructosamine associated with severity of coronary artery atherosclerosis in insulin resistant pigs fed a high fat/high NaCl diet," PloS one, vol. 10, No. 7, e0132302, 2015.
Owens, "Ultrasound-Enhanced Thrombolysis: EKOS EndoWave Infusion Catheter System," Seminars in Interventional Radiology, vol. 25, No. 1, pp. 1-5 (2008).

(56) References Cited

OTHER PUBLICATIONS

Owings, "FDA Clears EKOS EkoSonic Endovascular System," FDA News, www.fdanews.com/articles/164759-fda-clears-ekos-ekosonic-endovascular-system, pp. 1-2 (May 27, 2014).
Pajek et al., "High intensity focused ultrasound sonothrombolysis: the use of perfluorocarbon droplets to achieve clot lysis at reduced acoustic powers", Ultrasound Med Biol., Sep. 2014, vol. 40, No. 9, pp. 2151-2161.
Patel et al., "Adjunctive devices for non-balloon coronary interventional techniques and devices: rotational atherectomy, thrombectomy, cutting balloons, and embolic protection," The Interventional Cardiac Catheterization Handbook, pp. 159-178, Elsevier, 2018.
Previtali et al., "Risk factors for venous and arterial thrombosis," Blood Transfus., vol. 9, pp. 1-19 (2011).
Prokop et al., "Cavitational Mechanisms in Ultrasound-Accelerated Fibrinolysis," Ultrasound in Med. & Biol., vol. 33, No. 6, pp. 1-10 (2007).
Rao et al., "Trends in the prevalence and outcomes of radial and femoral approaches to percutaneous coronary intervention: a report from the National Cardiovascular Data Registry," JACC: Cardiovascular Interventions, vol. 1, No. 4, pp. 379-386, 2008.
Restenosis, [Online]. Available: http://chinesemedicinesalon.blogspot.com/2017/08/how-to-prevent-and-treat-coronary-in.html, Accessed on: May 2020.
Robert-Ebadi et al., "Use of anticoagulants in elderly patients: practical recommendations," Clinical Interventions in Aging, vol. 4, pp. 165-178 (2009).
Rojas et al., "Vaporization Detection Imaging: A Technique for Imaging Low-Boiling-Point Phase-Change Contrast Agents with a High Depth of Penetration and Contrast-to-Tissue Ratio," Ultrasound in Med. & Biol., vol. 45, No. 1, pp. 1-16 (2019).
Ross et al., "Curvilinear transurethral ultrasound applicator for selective prostate thermal therapy," Medical physics, vol. 32, No. 6, pp. 1555-1565, 2005.
Sakakura et al., "Controlled circumferential renal sympathetic denervation with preservation of the renal arterial wall using intraluminal ultrasound: a next-generation approach for treating sympathetic overactivity," EuroIntervention: Journal of EuroPCR in Collaboration with the Working Group on Interventional Cardiology of the European Societyof Cardiology, vol. 10, No. 10, pp. 1230-1238, 2015.
Sapareto et al., "Thermal Dose Determination in Cancer Therapy," International Journal of Radiation Oncology Biology Physics, vol. 10, No. 6, pp. 787-800, 1984.
Sen et al., "Mechanical Index," Anatol J Cardiol, vol. 15, pp. 334-336 (2015).
Serruys et al., "Percutaneous coronary intervention versus coronary-artery bypass grafting for severe coronary artery disease," New England Journal of Medicine, vol. 360, No. 10, pp. 961-972, 2009.
Shaw et al., "Pathophysiological mechanisms of high-intensity focused ultrasound-mediated vascular occlusion and relevance to non-invasive fetal surgery," J. R. Soc. Interface, vol. 11, pp. 1-17 (2014).
Sheeran et al., "Formulation and Acoustic Studies of a New Phase-Shift Agent for Diagnostic and Therapeutic Ultrasound," Langmuir, vol. 27, No. 17, pp. 1-23 (Sep. 6, 2011).
Shi et al., "Integrated histotripsy and bubble coalescence transducer for thrombolysis," Ultrasound Med Biol., vol. 44, No. 12, pp. 1-27 (Dec. 2018).
Shishitani et al., S. Yoshizawa, and S. I. Umemura, "Change in acoustic impedance and sound speed of HIFU-exposed chicken breast muscle," IEEE International Ultrasonics Symposium, pp. 1384-1387, 2010.
Siontis et al., "Percutaneous coronary interventional strategies for treatment of in-stent restenosis: a network meta-analysis," The Lancet, vol. 386, No. 9994, pp. 655-664, 2015.
Sommer et al., "Applicators for MR-Guided Ultrasonic Ablation of BPH," Invest Radiol., vol. 48, No. 6, pp. 1-18 (Jun. 2013).
Song et al., "Ultrasound Triggered Tumor Oxygenation with Oxygen-Shuttle Nanoperfluorocarbon to Overcome Hypoxia-Associated Resistance in Cancer Therapies," Nano Lett., vol. 16, pp. 1-9 (2016).
Sponer, "Theoretical estimation of the cavitation threshold for very short pulses of ultrasound," Ultrasonics, vol. 29, pp. 376-380 (Sep. 1991).
Steinberg et al., "Outcome differences with the use of drug-eluting stents for the treatment of in-stent restenosis of bare-metal stents versus drug-eluting stents," The American Journal of Cardiology, vol. 103, No. 4, pp. 491-495, 2009.
Stone et al., "Pulsed-high intensity focused ultrasound enhanced tPA mediated thrombolysis in a novel in vivo clot model, a pilot study," Thromb Res., vol. 121, No. 2, pp. 1-15 (2007).
Streiff et al., "Guidance for the treatment of deep vein thrombosis and pulmonary embolism," J Thromb Thrombolysis, vol. 41, pp. 1-36 (2016).
Suo et al., "Dynamic assessment of dual-frequency microbubble-mediated sonothrombolysis in vitro," Journal of Applied Physics, vol. 125, pp. 1-11 (Feb. 26, 2019).
Suo et al., "Microbubble mediated dual-frequency high intensity focused ultrasound thrombolysis: An In vitro study," Appl. Phys. Lett., vol. 110, pp. 1-5 (Jan. 10, 2017).
Suo et al., "Thrombolysis using multi-frequency high intensity focused ultrasound at MHz range: an in vitro study," Phys. Med. Biol., vol. 60, pp. 1-17 (2015).
Sutton et al. "Clot retraction affects the extent of ultrasound-enhanced thrombolysis in an ex vivo porcine thrombosis model," Ultrasound Med Biol., vol. 39, No. 5, pp. 1-23 (May 2013).
Szablowski et al., "Achieving Spatial and Molecular Specificity with Ultrasound-Targeted Biomolecular Nanotherapeutics," Acc Chem Res., vol. 52, No. 9, pp. 1-17 (Sep. 17, 2019).
Tachibana et al., "Albumin Microbubble Echo-Contrast Material as an Enhancer for Ultrasound Accelerated Thrombolysis," Circulation, vol. 92, No. 5, pp. 1-7 (1995).
Ter Haar, "HIFU tissue ablation: concept and devices," Therapeutic Ultrasound, pp. 3-20, Springer, Cham, 2016.
Ter Haar, "Therapeutic ultrasound," European Journal of Ultrasound, vol. 9, No. 1, pp. 3-9, 1999.
The Penumbra Pivotal Stroke Trial, "Safety and Effectiveness of a New Generation of Mechanical Devices for Clot Removal in Intracranial Large Vessel Occlusive Disease," pp. 1-8 (2009).
Van Ha, "Complications of Inferior Vena Caval Filters," Seminars in Interventional Radiology, vol. 23, No. 2, pp. 1-6 (2006).
Vanhille et al., "Numerical Simulations of the Nonlinear Interaction of a Bubble Cloud and High Intensity Focused Ultrasound Field," Acoustics, vol. 1, pp. 1-12 (2019).
Wang et al., "Comparative study of pulsed versus continuous high-intensity focused ultrasound ablation using in vitro and in vivo models," Journal of Ultrasound in Medicine, 2019.
Wang et al., "Disruption of microalgal cells using high-frequency focused ultrasound," Bioresource Technology, vol. 153, pp. 315-321, 2014.
Watson et al., "Thrombolysis for accurate deep vein thrombosis," Cochrane Database of Systematic Reviews, vol. 11, pp. 1-62 (2016).
Wright et al., "In Vitro and In Vivo High Intensity Focused Ultrasound Thrombolysis," Invest Radiol., vol. 47, No. 4, pp. 1-25 (Apr. 2012).
Wu et al., "Focused Ultrasound-Facilitated Brain Drug Delivery Using Optimized Nanodroplets: Vaporization Efficiency Dictates Large Molecular Delivery," Phys Med Biol., vol. 63, No. 3, pp. 1-24 (2019).
Wu et al., "Wide local ablation of localized breast cancer using high intensity focused ultrasound," Journal of Surgical Oncology, vol. 96, No. 2, pp. 130-136, 2007.
Xu et al., "Dependence of pulsed focused ultrasound induced thrombolysis on duty cycle and cavitation bubble size distribution," Ultrasonics Sonochemistry, vol. 22, pp. 1-7 2015).
Yang et al., "Effect of pulse repetition frequency of high-intensity focused ultrasound on in vitro thrombolysis," Ultrasonics Sonochemistry, vol. 35, pp. 1-9 (2017).
Zhang et al., "Histotripsy Thrombolysis on Retracted Clots," Ultrasound Med Biol., vol. 42, No. 8, pp. 1-35 (Aug. 2016).

(56) References Cited

OTHER PUBLICATIONS

Zhang et al., "Non-invasive Thrombolysis using Histotripsy beyond the "Intrinsic" Threshold (Microtripsy)," IEEE Trans Ultrason Ferroelectr Feq Control., vol. 62, No. 7, pp. 1-35 (Jul. 2015).
Zhang et al., "Noninvasive Thrombolysis using Microtripsy in a Porcine Deep Vein Thrombosis Model," Ultrasound Med Biol., vol. 43, No. 7, pp. 1-27 (Jul. 2017).
Zhang et al., "Non-invasive Thrombolysis using Microtripsy: A Parameter Study," IEEE Trans Ultrason Ferroelectr Freq Control., vol. 62, No. 12, pp. 1-34 (Dec. 2015).
Zhang et al., "Sonothrombolysis with Magnetic Microbubbles Under a Rotational Magnetic Field," Ultrasonics, vol. 98, pp. 1-26 (Sep. 2019).
Zhao et al., "Potential and problems in ultrasound-responsive drug delivery systems," International Journal of Nanomedicine, pp. 1-14 (Apr. 2013).
Zhong et al., "Low-Intensity Focused Ultrasound-Responsive Phase-Transitional Nanoparticles for Thrombolysis without Vascular Damage: A Synergistic Nonpharmaceutical Strategy," ACS Nano, vol. 13, pp. 1-17 (2019).

* cited by examiner

SYSTEMS AND METHODS FOR AN ULTRASOUND CATHETER

INCORPORATION BY REFERENCE TO ANY PRIORITY APPLICATIONS

This application claims priority to U.S. Provisional Application No. 63/375,038, filed on Sep. 8, 2022, the entirety of which is hereby incorporated by reference herein for all purposes. Any and all applications for which a foreign or domestic priority claim is identified in the Application Data Sheet as filed with the present application are hereby incorporated by reference under 37 CFR 1.57.

BACKGROUND

Field

The present disclosure relates generally to a catheter system, and more specifically, in certain embodiments, a catheter system with an ultrasound catheter that in certain embodiments utilizes an aspiration catheter or an aspiration sheath and/or a retriever catheter.

Description of the Related Art

Ultrasonic energy has been used to enhance the intravascular delivery and/or effect of various therapeutic compounds. In one system, ultrasound catheters are used to deliver ultrasonic energy and therapeutic compounds to a treatment site within a patient's vasculature. Such ultrasound catheters can comprise an elongated member configured to be advanced through a patient's vasculature and an ultrasound assembly that is positioned near a distal portion of the elongated member. The ultrasound assembly is configured to emit ultrasonic energy. Such ultrasound catheters can include a fluid delivery lumen that is used to deliver a therapeutic compound to the treatment site. In this manner, ultrasonic energy is delivered to the treatment site to enhance the penetration effect and/or delivery of the therapeutic compound.

SUMMARY

In certain aspects, a catheter system comprising: an aspiration catheter having a first end, a second end, and a body positioned between the first end and the second end; an ultrasound catheter having a proximal end, a distal end, and a body positioned between the proximal end and the distal end, the ultrasound catheter configured to insert through the body of the aspiration catheter; and a retriever catheter having a proximal end, a distal end, and a shaft positioned between the proximal end and the distal end, the retriever catheter configured to inserted through the body of the aspiration catheter.

In certain aspects, the aspiration catheter includes an expandable funnel at the second end.

In certain aspects, the expandable funnel is self-expandable.

In certain aspects, the distal end of the ultrasound catheter is configured to articulate.

In certain aspects, the ultrasound catheter further includes a knob and at least one pull wire, the at least one pull wire connect to the distal end of the ultrasound catheter and the knob.

In certain aspects, the knob is configured to rotate to articulate the distal end of the ultrasound catheter.

In certain aspects, the ultrasound catheter delivers a targeted ultrasound treatment.

In certain aspects, the ultrasound catheter further includes at least one lumen extending between the proximal end and the distal end.

In certain aspects, the distal end of the ultrasound catheter is configured to articulate between + or −180 degrees from a longitudinal axis of the ultrasound catheter.

In certain aspects, the ultrasound catheter is configured to deliver ultrasound at a frequency within the range of 450 kHz-850 kHz.

In certain aspects, a catheter system for treating a patient with a thromboembolism, the catheter system comprising: an aspiration catheter having a first end, a second end, and a body positioned between the first end and the second end; and an ultrasound catheter having a retriever extending from the ultrasound catheter, the ultrasound catheter configured to be inserted through the body of the aspiration catheter.

In certain aspects, the aspiration catheter includes an expandable funnel at the second end.

In certain aspects, a distal end of the ultrasound catheter is configured to articulate.

In certain aspects, the ultrasound catheter further comprises at least one wire connecting the distal end and a dial located on the ultrasound catheter, wherein the dial is configured to control articulation of the distal end.

In certain aspects, the ultrasound catheter delivers a targeted ultrasound treatment.

In certain aspects, wherein the expandable funnel is configured to self-expand.

In certain aspects, the retriever catheter includes a retriever located at a distal end of the retriever catheter that is configured to actively expand or collapse.

In certain aspects, the retriever catheter includes a knob able to control movement of the retriever.

In certain aspects, a method for treating a patient with a thromboembolism, the method comprising: advancing into a patient's vascular system an aspiration catheter having a first end, a second end, and a body positioned between the first end and the second end; advancing an ultrasound catheter having a proximal end, a distal end, and a lumen positioned between the proximal end and the distal end, through the aspiration catheter into a treatment site; with the ultrasound catheter delivering ultrasound energy and a therapeutic compound to the treatment site; and after treating at least a portion of the treatment site with ultrasound energy and a therapeutic compound, using a retriever to retrieve thromboembolism from the treatment site.

In certain aspects, delivering the therapeutic compound comprises delivering microbubbles to the treatment site through the lumen of the ultrasound catheter. In certain aspects, the therapeutic compound comprises delivering microbubbles mixed with a therapeutic compound to the treatment site through the lumen of the ultrasound catheter.

In certain aspects, the catheter includes an expandable funnel at the second end.

In certain aspects, the method further comprising articulating the distal end of the ultrasound catheter.

In certain aspects, the method further comprising articulating the ultrasound catheter and delivering a targeted ultrasound treatment to the treatment site.

In certain aspects, the method further comprising removing the ultrasound catheter from the aspiration catheter before advancing the retriever through the aspiration catheter and using the retriever to retrieve thromboembolism from the treatment site with the retriever.

In certain aspects, the method further comprising aspirating the thromboembolism at the treatment site though the aspiration catheter.

In certain aspects, a method for treating a patient with a thromboembolism, the method comprising: advancing the aspiration catheter having a first end, a second end, and a body positioned between the first end and the second end into a patient's vascular system; advancing an ultrasound catheter through the aspiration catheter and into a treatment site, the ultrasound catheter having a retriever catheter integrated within the ultrasound catheter configured to gather residual thrombus, the ultrasound catheter configured to insert through the aspiration catheter; emitting ultrasound energy to the treatment site; and retrieving the thromboembolism from the treatment site with the retriever catheter.

In certain aspects the aspiration catheter includes an expandable funnel at the second end.

In certain aspects, the method further comprising delivering microbubbles to the treatment site through a lumen of the ultrasound catheter.

In certain aspects, a distal end of the ultrasound catheter is configured to articulate.

In certain aspects, the method further comprising articulating the distal end of the ultrasound catheter and delivering a targeted ultrasound treatment to the treatment site.

In certain aspects, the method further comprising rotating the retriever catheter to control movement of a retriever to retrieve the thromboembolism from the treatment site.

In certain aspects, the method further comprising aspirating through the aspiration catheter and retracting the retriever catheter prior to aspirating the thromboembolism at the treatment site.

In certain aspects, a catheter system comprising: an aspiration catheter having a first end, a second end, and a body positioned between the first end and the second end; an ultrasound catheter having a proximal end, a distal end, and a body positioned between the proximal end and the distal end, the ultrasound catheter configured to insert through the body of the aspiration catheter, wherein the distal end of the ultrasound catheter is configured to articulate; and a retriever catheter having a proximal end, a distal end, and a shaft positioned between the proximal end and the distal end, the retriever catheter configured to be inserted through the body of the aspiration catheter.

In certain aspects, the aspiration catheter includes an expandable funnel at the second end.

In certain aspects, wherein the expandable funnel is self-expandable.

In certain aspects, the ultrasound catheter further includes at least one lumen positioned between the proximal end and the distal end.

In certain aspects, an ultrasound catheter system comprising: a body having a proximal end, a distal end, and a lumen from the proximal end to the distal end; and an ultrasound element, positioned at the distal end of the ultrasound catheter, wherein the distal end of the ultrasound catheter is configured to articulate.

In certain aspects, a catheter system comprising: an aspiration catheter having a first end, a second end, and a body positioned between the first end and the second end; an ultrasound catheter having a proximal end, a distal end, and a body positioned between the proximal end and the distal end, the ultrasound catheter configured to insert through the body of the aspiration catheter; and a retriever catheter having a proximal end, a distal end, and a shaft positioned between the proximal end and the distal end, the retriever catheter configured to insert through the body of the aspiration catheter.

In certain aspects, the aspiration catheter includes an expandable funnel at the second end.

In certain aspects, the expandable funnel is self-expandable.

In certain aspects, the distal end of the ultrasound catheter is configured to articulate.

In certain aspects, the ultrasound catheter further includes a knob and at least one pull wire, the at least one pull wire connect to the distal end of the ultrasound catheter and the knob.

In certain aspects, a method for treating a patient with a thromboembolism, the method comprising: advancing an ultrasound catheter having a proximal end, a distal end, and a lumen positioned between the proximal end and the distal end into a treatment site having a clot; delivering ultrasound energy and a therapeutic compound to the treatment site; after an initial treatment period of the clot, advancing the ultrasound catheter further in to clot; and articulating a distal end of the ultrasound catheter to provide targeted treatment to a segment of the treatment site with the ultrasound catheter.

In certain aspects, the method further comprising advancing an aspiration catheter into a patient's vascular system before advancing the ultrasound catheter and advancing the ultrasound catheter through the aspiration catheter and then into the treatment site.

In certain aspects, the aspiration catheter includes an expandable funnel at the second end.

In certain aspects, delivering ultrasound energy and therapeutic compound to the treatment site with the ultrasound catheter comprising delivering microbubbles and the therapeutic compound through a lumen of the ultrasound catheter and delivering ultrasound energy through an ultrasound element at the distal end of the ultrasound catheter.

In certain embodiments, a catheter system comprising: an aspiration catheter having a first end (which can also be referred to as a proximal end), a second end (which can also be referred to as a distal end), and a body positioned between the first end and the second end; an ultrasound catheter having a proximal end, a distal end, and a lumen positioned between the proximal end and the distal end, the ultrasound catheter configured to insert through the body of the aspiration catheter; and a retriever configured to insert through the lumen of the ultrasound catheter.

In certain embodiments, the aspiration catheter includes an expandable funnel at the second end.

In certain embodiments, the distal end of the ultrasound catheter is configured to articulate.

In certain embodiments, a catheter system comprising: an aspiration catheter having a first end, a second end, and a body positioned between the first end and the second end; and an ultrasound catheter having a retriever extending from the ultrasound catheter configured to gather, the ultrasound catheter configured to insert through the body of the aspiration catheter.

In certain embodiments, the aspiration catheter includes an expandable funnel at the second end.

In certain embodiments, a distal end of the ultrasound catheter is configured to articulate.

In certain embodiments, wherein the retriever is configured to self-expand.

In certain embodiments, wherein the retriever configured to actively expand or collapse.

In certain embodiments, the ultrasound catheter further comprises at least one wire connecting the distal end and a dial located on the ultrasound catheter, wherein the dial is configured to control articulation of the distal end.

In certain embodiments, wherein the retriever is configured to rotate to control movement of the retriever.

In certain embodiments, a method for treating a patient with a thromboembolism, the method comprising: advancing an ultrasound catheter having a proximal end, a distal end, and a lumen positioned between the proximal end and the distal end, the ultrasound catheter configured to insert through an aspiration catheter into a treatment site; emitting ultrasound energy to the treatment site; advancing the aspiration catheter having a first end, a second end, and a body positioned between the first end and the second end into a treatment site; aspirating a thromboembolism at the treatment site; and retrieving the thromboembolism from the treatment site with a retriever configured to insert through the lumen of the aspiration catheter.

In certain embodiments, the aspiration catheter includes an expandable funnel at the second end.

In certain embodiments, the distal end of the ultrasound catheter is configured to articulate.

In certain embodiments, a method for treating a patient with a thromboembolism, the method comprising: advancing an ultrasound catheter into a treatment site, the ultrasound catheter having a retriever catheter integrated within the ultrasound catheter configured to gather a thromboembolism, the ultrasound catheter configured to insert through an the aspiration catheter; emitting ultrasound energy to the treatment site; advancing an aspiration catheter having a first end, a second end, and a body positioned between the first end and the second end into the treatment site; aspirating a thromboembolism at the treatment site; and retrieving the thromboembolism from the treatment site with the mechanical catheter.

In certain embodiments, the aspiration catheter includes an expandable funnel at the second end.

In certain embodiments, a distal end of the ultrasound catheter is configured to articulate.

In certain embodiments, the retriever catheter rotates to control movement of a retriever to retrieve the thromboembolism from the treatment site.

In certain embodiments, the ultrasound catheter controls movement of a distal end of the ultrasound catheter to direct emission of ultrasound energy.

BRIEF DESCRIPTION OF THE DRAWINGS

Exemplary embodiments of systems and methods disclosed herein are illustrated in the accompanying drawings, which are for illustrative purposes only. The drawings comprise the following FIGURES, in which like numerals indicate like parts.

DETAILED DESCRIPTION

Figure 1:
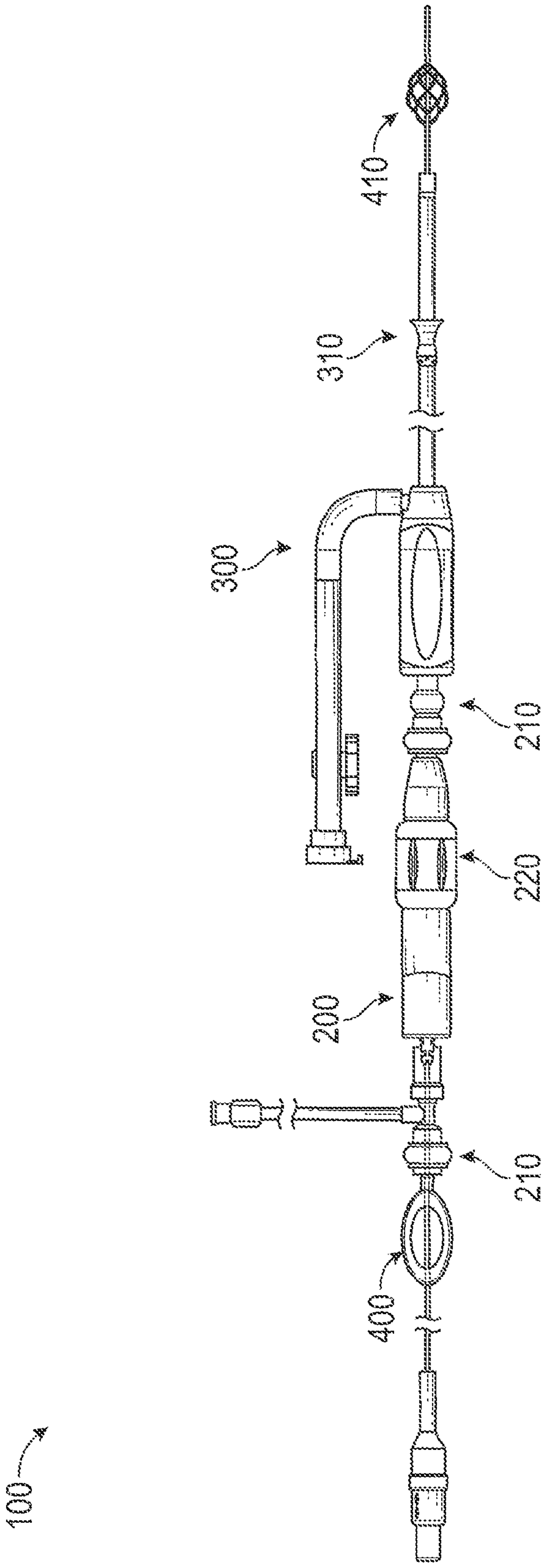
FIG. 1 illustrates a side view of an embodiment of a catheter system that includes an aspiration catheter, an ultrasound catheter and a retriever catheter.

As used herein, the term "ultrasonic energy" is used broadly, includes its ordinary meaning, and further includes mechanical energy transferred through compression and rarefaction waves with a frequency greater than about 20 kHz. Ultrasonic energy waves can have a center frequency between about 440 kHz and about 25 MHz. In some embodiments, ultrasound transducers may use a multiplicity of ultrasound energy frequencies to enhance cavitation. For example, multiple ultrasound transducers can be used in parallel or series to enhance cavitation. Additionally, ultrasound transducers may operate at different frequencies to produce a broadband of frequencies. As used herein, the term "catheter" is used broadly, includes its ordinary meaning, and further includes an elongated flexible tube configured to be inserted into the body of a patient, such as into a body part, cavity, duct or vessel (both arterial vessels and venous vessels). As used herein, the term "therapeutic compound" is used broadly, includes its ordinary meaning, and encompasses drugs, medicaments, dissolution compounds, genetic materials, and other substances capable of effecting physiological functions. A mixture comprising such substances is encompassed within this definition of "therapeutic compound". Specifically, for applications that treat human blood vessels that have become partially or completely occluded by plaque, thrombi (a thrombus), emboli or other substances that reduce the blood carrying capacity of a vessel, suitable therapeutic compounds include, but are not limited to, an aqueous solution containing heparin, urokinase, streptokinase, and/or rtPA and in certain aspects, "therapeutic compound" include but are not limited to micro or nano bubbles as described herein.

As expounded herein, ultrasonic energy is often used to enhance the delivery and/or effect of a therapeutic compound. For example, in the context of treating vascular occlusions, ultrasonic energy has been shown to increase enzyme mediated thrombolysis by enhancing the delivery of thrombolytic agents into a thrombus, where such agents lyse the thrombus by degrading the platelets of the thrombus. The thrombolytic activity of the agent is enhanced in the presence of ultrasonic energy in the thrombus because, for examples, the ultrasonic energy can create additional binding cites for the therapeutic compound. However, it should be appreciated that the present disclosure should not be limited to the mechanism by which the ultrasound enhances treatment unless otherwise stated. In other applications, ultrasonic energy has also been shown to enhance transfection of gene-based drugs into cells, and augment transfer of chemotherapeutic drugs into tumor cells. Ultrasonic energy delivered from within a patient's body has been found to be capable of producing non-thermal effects that increase biological tissue permeability to therapeutic compounds by up to or greater than an order of magnitude.

Use of an ultrasound catheter to deliver ultrasonic energy and a therapeutic compound directly to the treatment site mediates or overcomes many of the disadvantages associated with systemic drug delivery, such as low efficiency, high therapeutic compound use rates, and significant side effects caused by high dosage levels.

Microbubbles and/or metastable phase change nanodroplets may be added to the therapeutic compound. For example, the microbubbles and/or metastable phase change nanodroplets may be driven to cavitation by the ultrasound energy delivered by the ultrasound catheter. The microbubbles may be 500 nm-10 μm in size. In some aspects, the microbubbles may have a size of 1 μm-3 μm. Similarly, the metastable phase change nanodroplets may be 100 nm to 1 μm. In some aspects, the nanodroplets may have a size of 100 nm to 300 nm. The microbubbles and/or metastable phase change nanodroplets may be used in combination with or carry therapeutic agents, such as blood clot lysing agents. For example, when in combination with a therapeutic agent, the microbubbles and/or metastable phase change nanodroplets may be concentrated at 10^4 microbubbles/mL to 10^11 microbubbles/mL. In some aspects, the microbubbles and/or metastable phase change nanodroplets may be concentrated at approximately 10^8-10^9 microbubbles/mL. In aspects described herein, this mixture may contain 0 mg to 30 mg of rtPA. The microbubbles and/or nanodroplets can enhance the effectiveness of the ultrasound energy delivered to the treatment site. For example, ultrasound energy can be applied to the blood clot, including the microbubbles and/or metastable phase change nanodroplets within and/or surround the clot, causing the metastable phase change nanodroplets or microbubbles to oscillate, cavitate (both inertially and non-inertially), vaporize, and lyse the clot from within and/or surrounding the clot. Bioeffects may be achieved in result of the activation of the microbubbles from the ultrasound, which can include sonoporation, microstreaming and/or microjetting. The use of therapeutic agents (e.g., rtPA) in combination with microbubbles and/or metastable phase change nanodroplets to enhance sonothrombolysis can allow blood clots to be lysed more effectively and allows for the use of a reduced dosage of the therapeutic agent while the effectiveness of the treatment remains enhanced. The methods and systems for microbubbles and/or metastable phase change nanodroplets are further described in US 2020/0405258 and US 2021/0007759 the entirety of which is hereby incorporated herein by reference.

In some examples the catheter system can be used to treat the formation of a blood clot inside of a blood vessel (which can be referred to as a treatment site), obstructing the flow of blood through the circulatory system. Thrombosis can occur in veins (i.e., venous thrombosis) or in arteries (i.e., arterial thrombosis). In some examples, venous thrombosis leads to congestion of the affected part of the body, while arterial thrombosis may affect the blood supply to a part of the body which can lead to damage of the tissue supplied by the affected artery (e.g., ischemia and necrosis). Conditions that may arise from thrombosis and/or reduced blood flow can include deep vein thrombosis, peripheral artery disease, peripheral artery occlusion, and critical limb ischemia. In some examples, the catheter system can be used to treat treatment sites that include deep vein thrombosis, where a thrombus has formed in a deep vein, for example, in the legs or pelvis, or to treat pulmonary embolisms, where a thrombus has formed in the pulmonary vasculature. In some examples, the catheter system can be used to treat treatment sites that include arterial thrombosis, where a thrombus has formed in a coronary artery or in an artery that supplies the brain with blood. In some examples, the catheter system can be used to treat other treatment sites such as superficial vein thrombosis, where a thrombus has formed in a superficial vein, for example, in the legs. As will be explained below, in certain embodiments, a catheter system, that can include an ultrasound catheter can be used in combination with an aspiration catheter to provide suction (also referred to as aspiration) to the treatment site and assist in the removal of a clot (e.g., a thrombus resulting from thrombosis). For example, catheter system may be used to treat acute, subacute, and/or chronic clots. In certain aspects, the chronic clots may not include collagen. An acute clot may be softer or the softest of the three types of clots mentioned. Additionally, an acute clot may be the youngest (i.e., approximately 1-3 days) or newest clot and most porous clot. A chronic clot may be harder or the hardest of the three types of clots mentioned. Additionally, a chronic clot may be the oldest (i.e., approximately greater than 14 days) clot and least porous clot. A subacute clot may have a hardness, porosity, and age in between the characteristics described for an acute clot and a chronic clot. For example, a subacute clot may be approximately 3-14 days of age. While remnants of a thrombus may be left in the patient due to other forms of therapy, the use of an aspiration catheter can enhance the removal of the thrombus. In some embodiments, the catheter system can be used to minimize or eliminate the increased risk of bleeding complications by combining mechanisms and/or elements of action, which may be delivered through the catheter system. For example, in certain embodiments, the catheter (or catheter system) can form a multi-mechanism thrombectomy system that in certain embodiments utilizes microbubble-mediated cavitation as a mechanism of action to more effectively treat blood clots, without the increased risk of bleeding complications, and can combine four complementary mechanisms of action delivered through an integrated catheter system: (i) ultrasound, (ii) microbubbles (and/or nanodroplets), (iii) thrombolytic drug, and (iv) aspiration. Such a catheter system can also minimize blood loss and vessel wall damage arising from multiple passes of alternative thrombectomy devices. In certain embodiments, the catheter system can combine the benefits of mechanical thrombectomy and sonothrombolysis, while improving the reduction of thrombus burden and minimizing bleeding complications, blood loss, and vessel wall damage due to multiple passes resulting from alternative thrombectomy devices. Accordingly, the catheter or catheter system can form a multi-mechanism thrombectomy system that in certain embodiments utilizes microbubble-mediated cavitation as a mechanism of action to more effectively treat blood clots, without the increased risk of bleeding complications, and can combine four complementary mechanisms of action delivered through an integrated catheter system: (i) ultrasound, (ii) microbubbles (and/or nanodroplets), (iii) thrombolytic drug, (iv) aspiration and (v) a mechanical clot retriever. In certain embodiments, the catheter or catheter system can be used without microbubbles (and/or nanodroplets), In some aspects, an ultrasound catheter may be introduced to a treatment site within a patient. The treatment site may have a clot (e.g., a thrombus) that may require treatment. The ultrasound catheter may be introduced through the blood vessels until it reaches the treatment site. The ultrasound catheter may include an ultrasound transducer element which can deliver ultrasound energy directly to the treatment site to treat the thrombus. The ultrasound transducer element may come in direct contact with the thrombus at the treatment site and/or be positioned near or adjacent to the thrombus such that ultrasound energy can be directed towards the thrombus. The ultrasound transducer element may deliver ultrasound energy and the catheter can also deliver microbubbles and/or lytic to the thrombus before, after and/or during delivery of ultrasound energy. For a long segment of thrombus, as the thrombus begins to fragment or dissolve, the ultrasound catheter can be advanced through the thrombus site and continue to deliver ultrasound energy, microbubbles, and/or lytic to the thrombus. The ultrasound catheter can be advanced through the length of the thrombus until the length of the thrombus is minimized and the thrombus is entirely or almost entirely fragmented and/or dissolved. In some examples, a distal end of the ultrasound catheter may be configured to articulate. This may allow a targeted ultrasound treatment to be delivered to the treatment site. Articulation of the distal end of the ultrasound catheter may allow for the thrombus to be treated from different angles and/or may allow for a greater area of the treatment site to be treated more effectively. This articulation and targeted ultrasound treatment can occur as the ultrasound catheter is advanced through the clot. For example, after imaging and identifying residual clot, the distal end of the ultrasound catheter can be articulated to direct ultrasound energy to the identified residual clot. An advantage of targeted ultrasound can be the enhanced mechanical assistance/action in engaging thrombus for better/improved treatment which may allow new regions for treatment, more microchannels, and/or greater binding sites for lytic leading to improved performance and outcomes.

In some aspects, the ultrasound transducer element can operate at a frequency of approximately 440 kHz-25 MHz and in certain embodiments the frequency can be in the range of 450 kHz-850 kHz and in certain aspects 650 kHz. The frequency at which the ultrasound transducer element may operate at may be based on the location of the treatment site and/or the location of the thrombus within the treatment site. In some aspects, the frequency range of the ultrasound transducer may allow the generated ultrasonic waves to penetrate deeper into tissue where the treatment site may be located. In some aspects, the frequency range of the ultrasound transducer may allow the generated ultrasonic waves to penetrate a shallow depth of the tissue where the treatment site may be located.

In some aspects, once the ultrasound catheter delivers treatment to the treatment site (which can include an obstruction, such as a clot or thrombosis, to the flow of blood through the circulatory system), the ultrasound catheter may be removed from the treatment site. In some aspects, the ultrasound catheter may remain at the treatment site. An aspiration catheter or aspiration sheath or sheath (used interchangeably throughout) may be advanced into the patient's vascular system and advanced towards the treatment site. In some aspects, the aspiration catheter may be advanced to an area near the treatment site. In some aspects, the aspiration catheter may be advanced to an area between an insertion site and the treatment site. In some aspects, an aspiration catheter can be used to gain access from outside the body to inside the body and in such embodiments, the aspiration catheter can be used as an access sheath through which other devices can be inserted. In some aspects, the aspiration catheter can be used in treating deep vein thrombosis. In some aspects, an aspiration catheter can be used to track location of the treatment provided (e.g., a pulmonary embolism). In some aspects, this may be used when treating a pulmonary embolism. The aspiration catheter or aspiration sheath or sheath are used interchangeably herein in all embodiments and aspects. The aspiration catheter may be used in combination with a retriever catheter and the ultrasound catheter. The aspiration catheter can be referred to as an aspiration sheath and in certain embodiments aspiration can be applied to the vascular system through the aspiration catheter, however, in some aspects the aspiration need not be applied and the aspiration catheter/sheath can be used as an introducer catheter to deliver other instruments and catheter through the lumen of the aspiration sheath/catheter. In some aspects, the aspiration catheter may be introduced into the patient's vascular system prior to the ultrasound catheter being introduced into the patient such that the ultrasound catheter is advanced through the aspiration catheter and then advanced to the treatment site. In this manner, the ultrasound catheter may be inserted through the aspiration catheter. In some aspects, the aspiration catheter may include a funnel with an expanded opening that can guide elements of the fragmented and/or dissolved thrombus as the treatment site is aspirated. In some aspects the retriever catheter may be inserted through the ultrasound catheter. The retriever catheter may extend passed the distal end of the ultrasound catheter. In other aspects, the ultrasound catheter may be removed from the aspiration catheter to allow for the retriever catheter to be inserted through the aspiration catheter. This may be further described below with reference to FIGS. 9A and 9C. The retriever catheter may include a retriever that can engage the thrombus and/or elements of the fragments and/or dissolved thrombus. The retriever may break the thrombus further apart and/or dislodge it from the vessel wall to remove the thrombus from the treatment site as the retriever is withdrawn into the aspiration catheter. The retriever can capture the thrombus and the fragmented and/or dissolved thrombus elements. As the retriever removes the thrombus and the fragmented and/or dissolved thrombus elements from the treatment site, the aspiration catheter can be used to aspirate the area and/or treatment site. This can help to ensure the treatment site is effectively treated and the thrombus is effectively removed from the treatment site. Once the retriever removes the thrombus from the treatment site and the aspiration catheter can aspirate the area and/or the treatment site before, during, and/or after the removal of the thrombus. In other aspects, the aspiration catheter may not aspirate the area or treatment site. In such embodiments, the aspiration catheter or sheath can be used to provide access to the vascular system and can be used to introduce other devices (such as, for example, the ultrasound catheter or retriever catheter). Aspiration of the area and/or treatment site may be based on the effectiveness of the removal of thrombus by the retriever. The combination of catheters can help to maximize the effectiveness of the removal of the thrombus from the treatment site and restore blood flow to the blood vessels. In certain embodiments described herein, features of the aspiration catheter and/or retriever can be combined with the ultrasound catheter. For example, in certain embodiments, the ultrasound catheter can be advanced through the aspiration catheter such that the aspiration catheter is positioned within the patient during treatment with the ultrasound, drug (e.g., lytic) and/or microbubbles (and/or nanodroplets). In such embodiments, the ultrasound catheter can be removed from the aspiration catheter and then the retriever catheter can be advanced through the aspiration catheter after removal of the ultrasound catheter. In other embodiments, a retriever can be positioned on the ultrasound catheter and the retriever on the ultrasound catheter can be used to withdraw and/or dislodge the clot after treatment.

In some aspects, an aspiration catheter (according to aspects described herein) may be introduced into the vascular system through an access site and in certain embodiments advanced towards the treatment site and in certain embodiments advanced to the treatment site (which may include an obstruction, as described above, to the flow of blood through the circulatory system). After introduction of the aspiration catheter into the vascular system, an ultrasound catheter (according to aspects described herein) may be introduced to the treatment site as well. In certain aspects, the ultrasound catheter and aspiration catheter can be introduced together into the vascular system. The ultrasound catheter may be advanced through the aspiration catheter to then be introduced to the treatment site. The distal end of the aspiration catheter can be positioned near the treatment site or further away from the treatment site, such as, closer to the access site. The ultrasound catheter may deliver microbubbles and/or metastable phase change nanodroplets and rtPA or other therapeutic compounds (e.g., a lytic) to the treatment site. The microbubbles and/or metastable phase change nanodroplets and rtPA or other therapeutic compounds (e.g., a lytic) can be delivered through a lumen in the ultrasound catheter and/or through another passage in the catheter system. This can allow for treatment of the thrombus located at the treatment site. For example, delivering microbubbles and/or metastable phase change nanodroplets can create microchannels within the thrombus. The ultrasound catheter can then deliver ultrasound energy or ultrasound treatment to the thrombus. The ultrasound catheter can continue to deliver treatment to the thrombus (ultrasound and/or microbubbles and/or metastable phase change nanodroplets and rtPA or other therapeutic compounds (e.g., a lytic) to the treatment site) as it is advanced through the length of the thrombus. For example, in certain aspects, the ultrasound catheter is first positioned near the thrombus or within the beginning of the thrombus and then after treatment with ultrasound and a therapeutic compound begins, the ultrasound catheter can be advanced into (or further into) the thrombus and further treatment can be provided with ultrasound and a therapeutic compound. Ultrasound can be provided within the frequency and power ranges described herein. For example, in some aspects, the ultrasound transducer element can operate at a frequency of approximately 440 kHz-25 MHz and in certain embodiments the frequency can be in the range of 450 kHz-850 kHz and in certain aspects 650 kHz. Advantageously, the microbubbles and/or metastable phase change nanodroplets and rtPA or other therapeutic compounds (e.g., a lytic) in combination with the ultrasound may aid in boring a hole or passage through the clot. For example, the ultrasound catheter can be advanced 25% through length of thrombus, 50% through length of thrombus, 100% through length of thrombus and deliver treatment all throughout. The ultrasound catheter can then be removed from the treatment site. A retriever catheter (according to aspects described herein) may then be introduced to the treatment site. The retriever catheter can be advanced through the aspiration catheter to be introduced to the treatment site. The retriever catheter may be advanced to the most outer end of the treatment (e.g., entirely or substantially through the clot) site and deploy a retriever. The retriever may capture the degraded and/or residual thrombus at the treatment site. The retriever catheter may then retract the retriever from the treatment site and into the aspiration catheter. The aspiration catheter may then aspirate the area and/or treatment site to direct the degraded and/or residual thrombus into the aspiration catheter. In other aspects, the aspiration catheter may not aspirate the area or treatment site. Aspiration of the area and/or treatment site may be based on the effectiveness of the removal of thrombus by the retriever. The advancement of the retriever catheter, deployment of the retriever, retraction of retriever, and aspiration of the treatment site may be repeated until the treatment site is free or mostly free of thrombus. In certain aspects, the retriever catheter can be inserted through the ultrasound catheter or alongside the ultrasound catheter such that the ultrasound catheter does not need to be removed before the retriever catheter is used to remove the clot.

The techniques disclosed herein can find utility with a wide variety of ultrasound catheters in addition to the ultrasound catheter embodiments described here. Certain of the techniques disclosed herein are compatible with ultrasound catheters and/or aspiration catheters that would be unable to generate cavitation at an intravascular treatment site but for the use of such techniques.

With reference to the illustrated embodiments, FIG. 1 illustrates an example of a catheter system 100 configured for use at a treatment site within a patient. For example, in certain embodiments, the catheter system 100 includes an ultrasound catheter 200, an aspiration catheter 300, and a retriever catheter 400. The catheter system 100 can be used to deliver ultrasound energy to a treatment site within a patient to assist in dissolving or lysing a thrombus located at the treatment site. The catheter system 100 can also be used to aspirate the thrombus at the treatment site. Additionally or alternatively, the catheter system 100 can be used to mechanically retrieve the thrombus from the treatment site with the retriever catheter 400. The catheter system 100 can also include at least one valve 210 that may be used to connect the various elements of the catheter system 100. In some examples, the valve can include a Tuohy-Borst adapter, or a hemostasis valve, which can minimize fluid loss during use of the catheter system 100. In some examples, the hemostasis valve can include side port tubing. The aspiration catheter 300 can include a flared end 310. In some examples, the flared end 310 can aspirate a greater area of the thrombus at once and can aid in withdrawing a clot or thrombus retrieved by the retriever catheter 400 into the aspiration catheter 200. The flared end 310 may be a funnel that is connected or bonded to the aspiration catheter 300.

In some examples, the ultrasound catheter 200 can include an ultrasound element (described in more detail below) that may deliver ultrasound energy to a treatment site within a patient. In some examples, the ultrasound catheter 200 can include a handle 220, which can control the deflection of a distal tip of the ultrasound catheter 200 (as will be explained in more detail below). This may allow the catheter system 100 to more accurately direct or control where ultrasound energy is delivered. Additionally, this may allow the ultrasound catheter 200 to more effectively be advanced to the treatment site and the length of the thrombus. This may further allow the ultrasound catheter 200 to more effectively deliver ultrasound treatment to a thrombus that is relatively more lodged in the blood vessel.

In some examples, the retriever catheter 400 can include a retriever 410 located at a distal end of the retriever catheter 400. As further described below, in certain embodiments, the retriever catheter 400 may include an actuator that can be rotated (or otherwise actuated) to cause the retriever 410 to selectively expand or collapse. The expansion and collapsing of the retriever 410 may assist in the removal of the blood clot from the treatment site of the patient. In certain embodiments, the retriever 410 can be self-expandable once it is advanced past the distal end of the aspiration catheter 200 or ultrasound catheter 300.

Figure 1A:
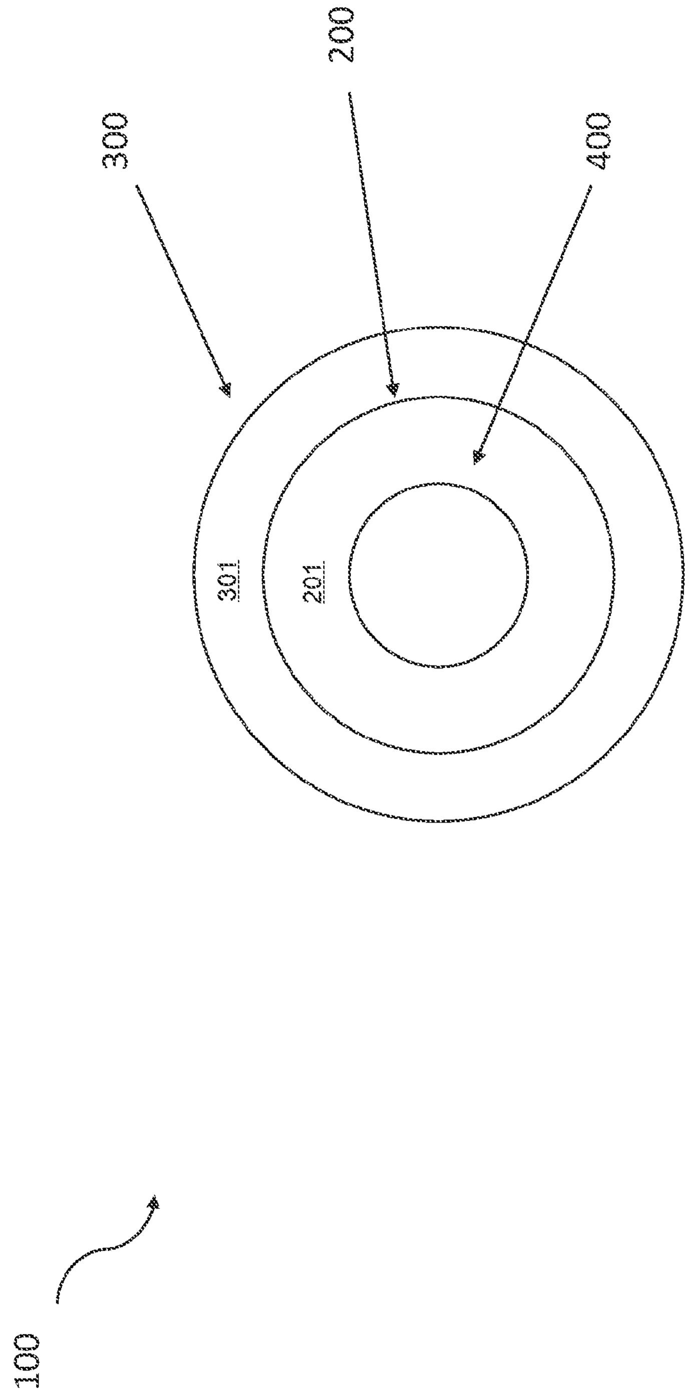
FIG. 1A illustrates a cross sectional view of the catheter system.

With reference to the illustrated embodiments, FIG. 1A illustrates a schematic cross section of the catheter system 100 with reference to FIG. 1. As shown, the aspiration catheter 300, ultrasound catheter 200, and retriever catheter 400 may be concentric. In some examples, the aspiration catheter may include at least one aspiration lumen 301 (schematically illustrated in FIG. 1A). In some examples, the ultrasound catheter 200 may be inserted through the at least one aspiration lumen 301 of the aspiration catheter 300. In some examples, the ultrasound catheter 200 may include at least one lumen 201 (schematically illustrated in FIG. 1A) which can be used to deliver a therapeutic compound to the treatment site. The lumen 201 can also be used to advance the ultrasound catheter over a guidewire. In certain aspects, the ultrasound catheter can include multiple lumens. In some examples, the retriever catheter 400 may be inserted through the at least one lumen 201. For example, the retriever catheter 400 may be inserted into a proximal end of the ultrasound catheter 200 and extend through the at least one lumen 201 of the ultrasound catheter 200. In other examples, the retriever catheter 400 may be inserted through the at least one aspiration lumen 301 as described above. For example, the retriever catheter can be configured to be inserted into a proximal end of the aspiration catheter 300 and extend through the aspiration lumen 301 after the ultrasound catheter 200 is removed from the aspiration catheter 300. In other aspects, the retriever catheter can be inserted along the side of the ultrasound catheter 200 with the aspiration lumen 301. The retriever catheter 400 may extend through the at least one lumen 201 of the ultrasound catheter 200 and extend passed a distal end of the ultrasound catheter 200. Similarly, the ultrasound catheter 200 may be inserted into a proximal end of the aspiration catheter 300. The ultrasound catheter 200 may extend through the aspiration lumen 301 of the aspiration catheter 300 and extend passed a distal end of the aspiration catheter 300. In some examples, the retriever catheter 400 may be inserted through the at least one lumen 201 of the ultrasound catheter 200 as the ultrasound catheter 200 is inserted through the aspiration lumen 301 of the aspiration catheter 300. In some examples, the retriever catheter 400 may have a larger diameter and be configured to extend passed the aspiration catheter 300 when the ultrasound catheter 200 is removed from the aspiration catheter.

Figure 2:
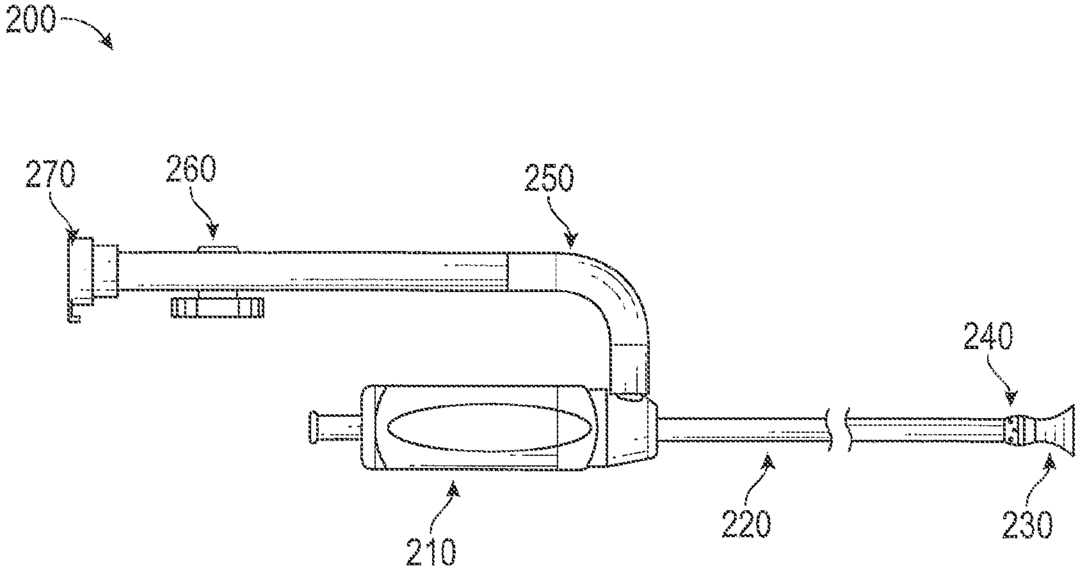
FIG. 2 illustrates a side view of the aspiration catheter of FIG. 1.

With reference to the illustrated embodiments, FIG. 2 illustrates the aspiration catheter 200 as referred to in FIG. 1, but now shown in isolation. As shown, the aspiration catheter 200 has a first (distal) end, a second (proximal) end, a handle 210 at the proximal end, a body formed by a shaft or extrusion 220 positioned between the distal and proximal end of the aspiration catheter 200, and an expandable funnel or flared end 230 at the second (distal) end of the aspiration catheter 200. The extrusion 220 can extend through the handle 210 and connect to a distal interface 240 of the aspiration catheter 200. The distal interface 240 can be molded and bonded to the extrusion 220 and the flared end 230. In some examples, the distal interface 240 can be radiopaque. The flared end 230 can be bonded to the distal interface 240. In some examples, the flared end 230 may have a first diameter and a second diameter; the first diameter may be smaller than the second diameter. The flared end 230 may include a body that connects the first diameter to the second diameter. In some examples, the flared end 230 can function as a lead-in feature of the aspiration catheter 200. The flared end 230 can help to maximize the amount of thrombus that is removed from the treatment site. In some examples, the flared end 230 can be collapsible and expand to the treatment site of the patient. For example, the flared end 230 can expand to a vessel wall of the treatment site of the patient. This can help to ensure the thrombus and/or debris is effectively removed from the treatment site. In some examples, the flared end 230 can direct aspiration of the aspiration catheter. For example, the flared end 230 can be open or closed to direct the aspiration. In some examples, the flared end 230 can be actively deployable. In some examples, the flared end (expandable funnel) 230 can be self-expandable. In some examples, the flared end 230 may include radiopaque features. In some examples, the flared end 230 may include nitinol. In some examples, the flared end 230 may have finger-like structures that may be connected by film which may or may not be perforated. In some examples, the flared end 230 may be actuated by use of an outer cover or tube that may slide over or cover and cause the finger-like structures to draw closer together until the structures are in an isodiametric arrangement. The aspiration catheter can also include tubing 250, a one-way stop cock 260, and a vacuum syringe port 270 to assist in aspiration. In some examples, the tubing 250 can include flexible, large bore tubing. The aspiration catheter 200 defines an aspiration lumen (not shown) that can extend through the aspiration catheter 200.

Figure 2A:
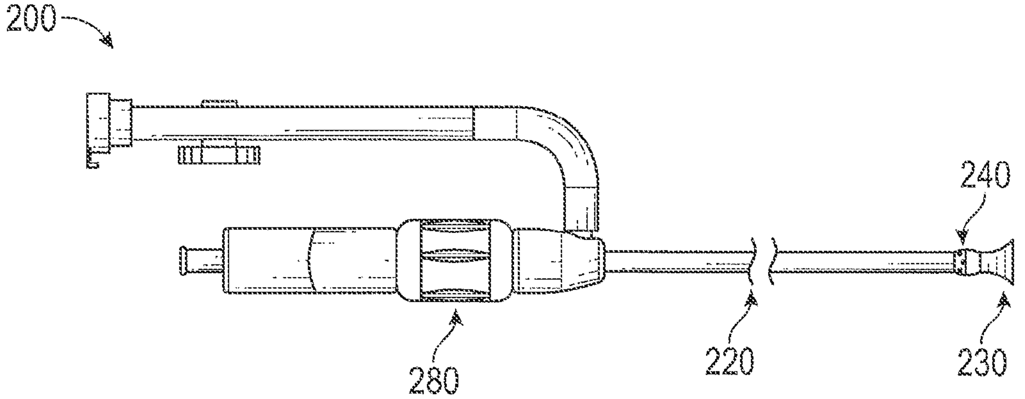
FIG. 2A illustrates another embodiment of an aspiration catheter that can be used with the ultrasound catheter system of FIG. 1.

With reference to the illustrated embodiments, FIG. 2A illustrates an alternative embodiment of the aspiration catheter 200 as referred to in FIG. 2. As shown, the aspiration catheter 200 can include a knob 280 that may articulate a distal interface 240 of the aspiration catheter. The extrusion 220 can include pull wires that connect to the knob 280 and the distal interface 240 that may allow for 180-degree articulation of the aspiration catheter 200 and/or active expansion and/or contraction of the distal end of the aspiration catheter 200. In some examples, the distal interface 240 can be molded and bonded to the extrusion 220 and the flared end 230.

Figure 3:
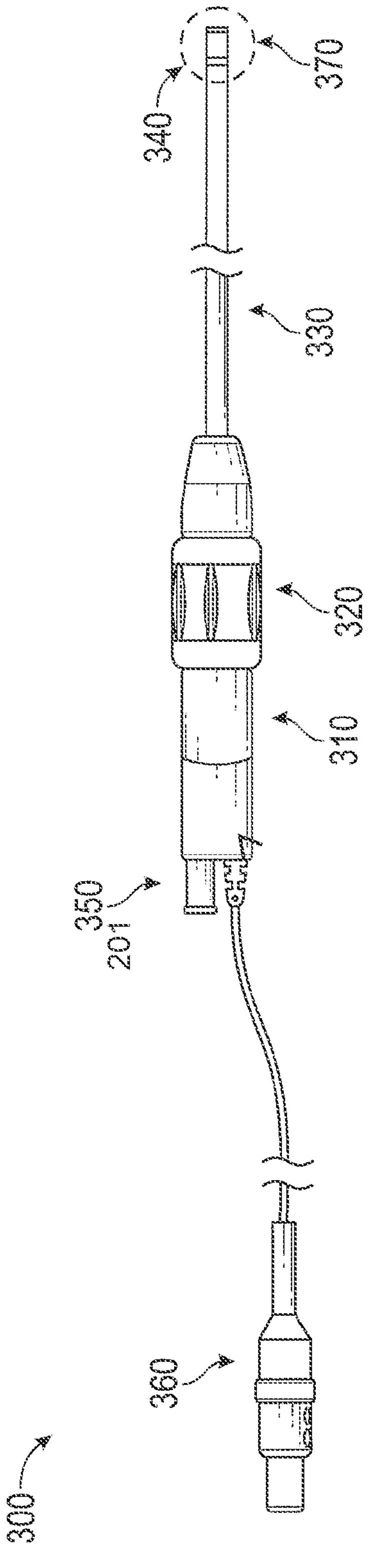
FIG. 3 illustrates a side view of the ultrasound catheter of FIG. 1.

With reference to the illustrated embodiments, FIG. 3 illustrates an ultrasound catheter 300 as referred to in FIG. 1, but now shown in isolation. As shown, the ultrasound catheter 300 can include the handle 310, a knob 320, and an extrusion 330. The extrusion 330 can have a proximal end 340 and a distal end with a body positioned between the distal end and proximal end 340. The distal end 340 may be articulated by rotation of knob 320. In some examples, the handle 310 may have a length of approximately 3.0 in.-5.0 in. This can allow for a steerable ultrasound catheter. For example, a user can rotate the knob 320 (e.g., clockwise or counterclockwise direction) to control the deflection of the distal end 340. The articulation of the distal end 340 can better direct the delivery of the ultrasound energy to the treatment site within the patient. For example, articulation of the distal end 340 can help to better dislodge the thrombus from the treatment site by better targeting ultrasound towards a portion of the thrombus that may require additional treatment to dislodge or fragment. Additionally, articulation of the distal end 340 can better target the thrombus located in the treatment site as well. This can allow for treatment of the thrombus by visualization and/or target searching. This technique allows for localized treatment and minimizes or limits any potential for damage to healthy or surrounding tissue. The extrusion 330 can be a multi-lumen extrusion that includes one or more pull-wires 335 extending along the length of the catheter configured to articulate the distal end 340 by connecting the distal end 340 and the knob 320. The pull-wires 335 can allow articulation of the distal end 340 by approximately + or −180 degrees from the longitudinal axis of the catheter and in some embodiments + or −45 degrees longitudinal axis of the catheter. FIG. 3C schematically illustrates pull wires 335 which are connected to the distal end 340 for providing articulation. In some examples, the ultrasound catheter 300 can further include at least one lumen 201 and a pigtail cable 360 connected to a proximal end of the ultrasound catheter 300. The lumen 201, for example, a female luer, can extend through the ultrasound catheter 300 to allow for an introduction of fluids to the patient. For example, the fluids may consist of a therapeutic compound, flush, radiopaque contrast agents, etc. In some examples, the fluids may enter the ultrasound catheter through the at least one lumen 201 or another lumen of the ultrasound catheter. The lumen 201 may be welded or otherwise secured to the catheter 300. In certain embodiments, the ultrasound catheter 300 may have a length of approximately 1.0 m-1.5 m and a diameter of 0.6 in-0.8 in. As shown in FIG. 3, and further described in FIG. 3A below, the ultrasound catheter 300 can include an ultrasound element (also referred to herein as an ultrasound radiating element) 370 connected to the distal end 340.

Figure 3A:
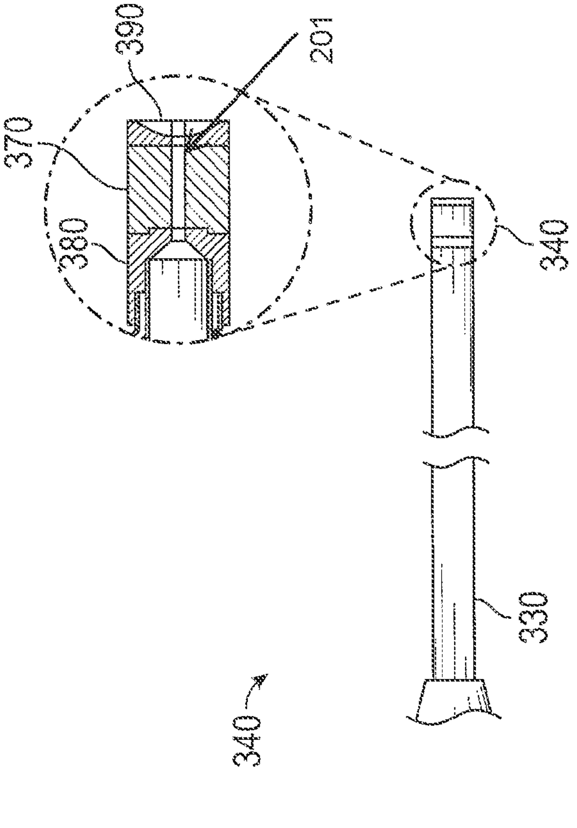
FIG. 3A illustrates an enlarged view of a distal tip of the ultrasound catheter of FIG. 3.

With reference to the illustrated embodiments, FIG. 3A illustrates a zoomed in view of the distal end 340 as referred to in FIG. 3. As shown, the ultrasound element 370 can be bonded to a molded interface 380 which may be bonded to the extrusion 330. As explained above, the bonding can assist in allowing articulation of the distal end 340. This connection can further provide fluid ports for the distal end 340. In some examples, the ultrasound element 370 can be cylindrical and hollow and include a concave lens 390. In certain embodiments, the concave lens 390 may assist in focusing the ultrasonic field to assist in treatment or removal of the thrombus at the treatment site.

With continued reference to FIG. 3A, the distal end 340 of the ultrasound catheter 300 can include the ultrasound radiating element 380 (also referred to herein as an ultrasound element). In the illustrated embodiment, the ultrasound radiating element 370 comprises an ultrasound transducer, which may be radiopaque, which converts energy, for example, electrical energy into ultrasound energy. In a modified embodiment, the ultrasound energy can be generated by an ultrasound transducer that is remote from the ultrasound radiating element 380 and the ultrasound energy can be transmitted via, for example, a wire to the ultrasound radiating element 370. In some examples, ultrasound energy may be radiated by use of a vibrating wire, transducer or a laser. As mentioned above, in the illustrated embodiment, ultrasound energy is generated from electrical power supplied to the ultrasound radiating element 370. The electrical power can be supplied through a connector, which is connected to a pair of wires 365 (shown schematically in FIG. 3D) that extend through the body of the ultrasound catheter 300. In the illustrated arrangement, the first wire 362 can be connected to the hollow center of the ultrasound radiating element 370 while the second wire 364 is connected to the outer periphery of the ultrasound radiating element 380. Thus, in the illustrated embodiment, the ultrasound catheter includes at least one lumen 201 extending through the catheter and through the ultrasound radiating element 380. In certain aspects, a guidewire can be inserted through the at least one lumen 201 or another lumen of the ultrasound catheter. In certain aspects, the therapeutic compound and/or microbubbles and/or nanobubbles can be delivered to the treatment site through the at least one lumen 201 of the ultrasound catheter 300, or another lumen of the ultrasound catheter. The lumen 201 can also be used to advance the ultrasound catheter over a guidewire in certain embodiments. In the illustrated arrangement, a fenestrated ultrasound radiating element 370 can be used. In other aspects, a solid ultrasound radiating element 370 may be used, in which case the first wire can be connected to the outer periphery of the of the ultrasound radiating element 370. The ultrasound radiating element 370 is preferably, but not limited to, a transducer formed of a piezoelectric ceramic oscillator or a similar material. Piezoelectric ceramic oscillators typically comprise a crystalline material, such as quartz, that can change shape when an electrical current is applied to the material. This change in shape, when made oscillatory by an oscillating driving signal, can create ultrasonic sound waves. In other embodiments, ultrasonic energy can be generated by an ultrasonic transducer that is remote from the ultrasound radiating member, and the ultrasonic energy can be transmitted, via, for example, a wire that is coupled to the ultrasound radiating member such as that described in U.S. Pat. No. 8,668,709, the entirety which is hereby incorporated by reference herein. In other embodiments, the ultrasound radiating element can be a photoacoustic ultrasound element in which a material emits pressure waves in response to being illuminated by a light source (e.g., a laser). For example, the photoacoustic ultrasound element can be formed of a formed from a light-absorbing material and a thermal expansion material that can be in optical communication with a light guide such that light is absorbed by the photoacoustic transducer and converted into acoustic wave as the transducer changes shape such as described in U.S. Pat. No. 11,622,779, the entirety of which is hereby incorporated by reference herein.

While not illustrated, the ultrasound catheter 300 may include at least one temperature sensor and/or force sensor along the distal end. The temperature sensor and/or force sensor can be located on or near the ultrasound radiating element 370. Suitable temperature sensors include but are not limited to, diodes, thermistors, thermocouples, resistance temperature detectors (RTDs), and fiber optic temperature sensors such as a Fabry-Perot sensor that uses thermochromic liquid crystals. Suitable force sensors include, among others, Fabry-Pérot, fiber Bragg grating, resistors, load cells, and strain gauges. The temperature sensor and/or force sensor can operatively connect to a control box (not shown) through a control wire, which extends through the ultrasound catheter. The temperature sensor can be used to sense the temperature of the ultrasound radiating element 370 which can help to limit damage to the surrounding tissue.

Figure 3B:
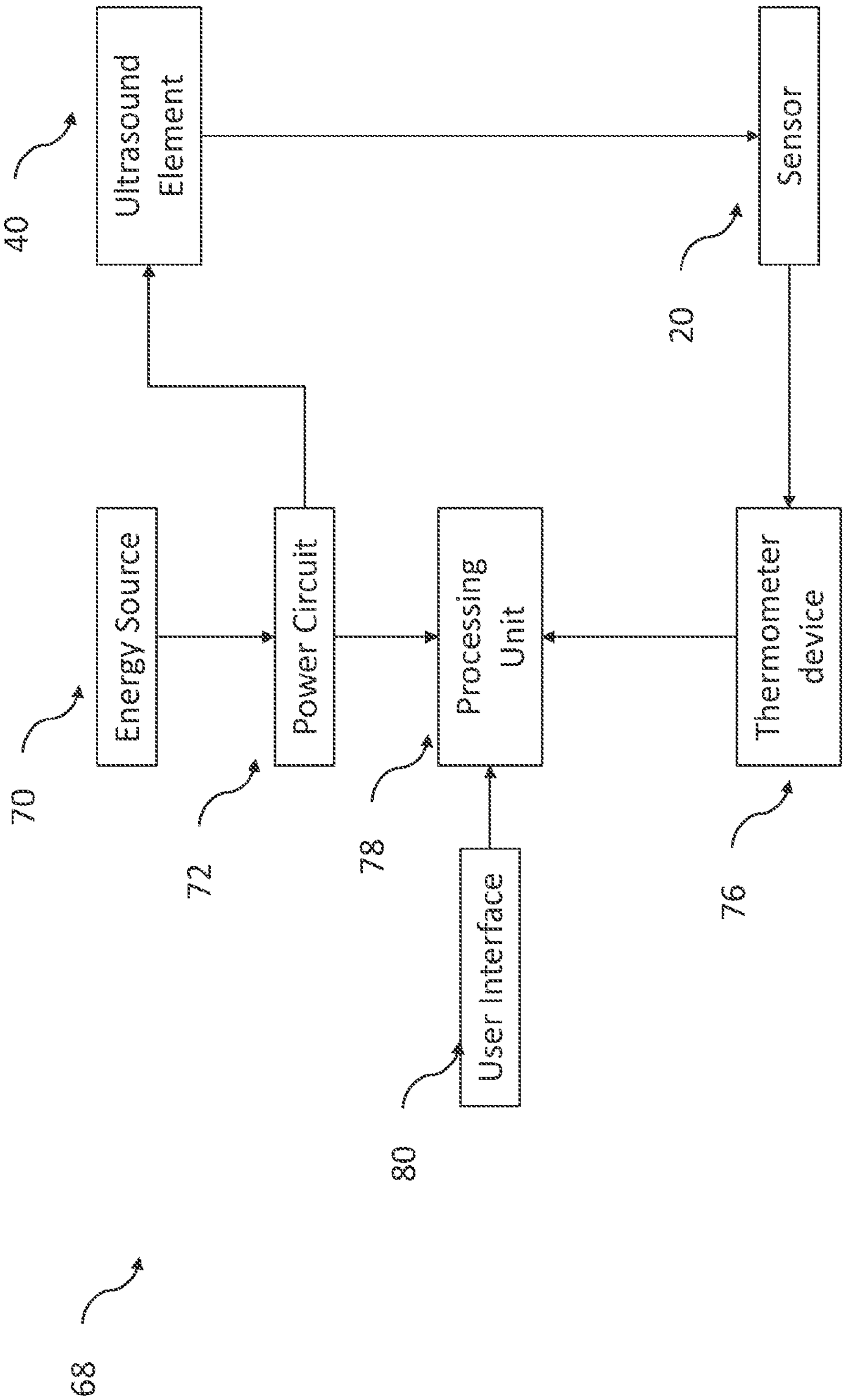
FIG. 3B is a block diagram of a feedback control system for use with the ultrasound catheter of FIG. 3.
Figure 3C:
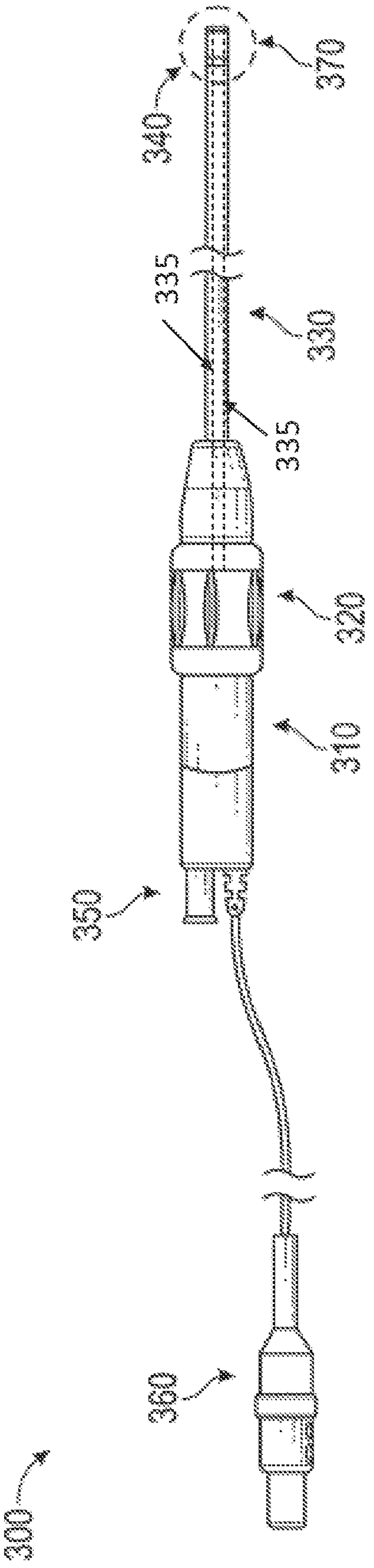
FIG. 3C is a schematic illustration of control wires for articulating the ultrasound catheter of FIG. 3.
Figure 3D:
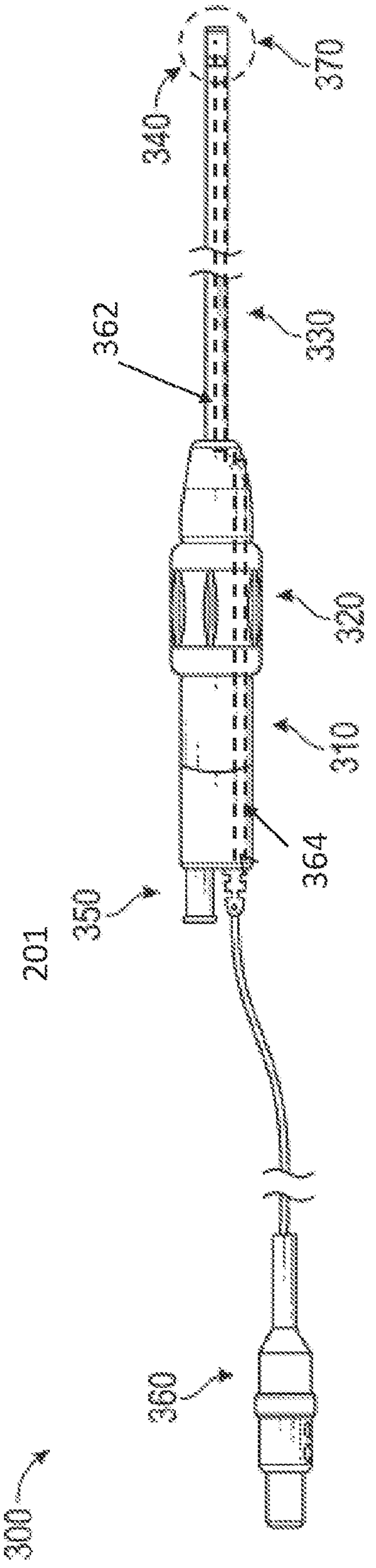
FIG. 3D is a schematic illustration of an electrical connection to an ultrasound element of the ultrasound catheter of FIG. 3.

With reference to the illustrated embodiments, FIG. 3B illustrates a feedback control system 68 that can be used with the ultrasound catheter as described with reference to FIG. 3 and FIG. 3A. The feedback control system 68 can allow the temperature at a temperature sensor 20 to be monitored and allows the output power of ultrasound radiating element to be adjusted accordingly. The feedback control system 68 can include an energy source 70 (i.e., ultrasound energy source) and power circuits 72 that may be coupled to the ultrasound radiating element 40. A thermometer device 76 may be coupled to the temperature sensor 20 in the body 12. A processing unit 78 may be coupled to the power calculation device 74, the power circuits 72 and a user interface 80. The thermometer device 76 may measure the temperature at the location of the temperature sensor. The measured temperature may be received by the processing unit 78 to then be displayed to the user. Additional sensors (e.g., a force sensor) can also be connected to the processing unit 78.

The power circuits 72 may adjust the power level, frequency, voltage, phase and/or current of the electrical energy supplied to the ultrasound radiating element 40 from the energy source 70. For example, the power may be reduced if the measured temperature at the location of the temperature sensor is higher than the desired or safe temperature. Similarly, for example, the power may be increased if the measured temperature at the location of the temperature sensor is lower than the desired temperature. As the power is adjusted, the processing unit 78 may monitor the temperature sensor 20.

In general, the feedback control system can be used to more efficiently provide treatment to the treatment site by helping to ensure the ultrasound radiating element remains at a desired temperature so that surrounding tissue is not damages and can remain at a desired temperature.

Additionally, the feedback control system may control the mode in which the ultrasound radiating element may operate in. For example, the ultrasound radiating element may operate in a pulsed mode or a continuous mode. The mode in which the ultrasound radiating element operates in may determine the power that is supplied to the ultrasound radiating element.

Figure 4:
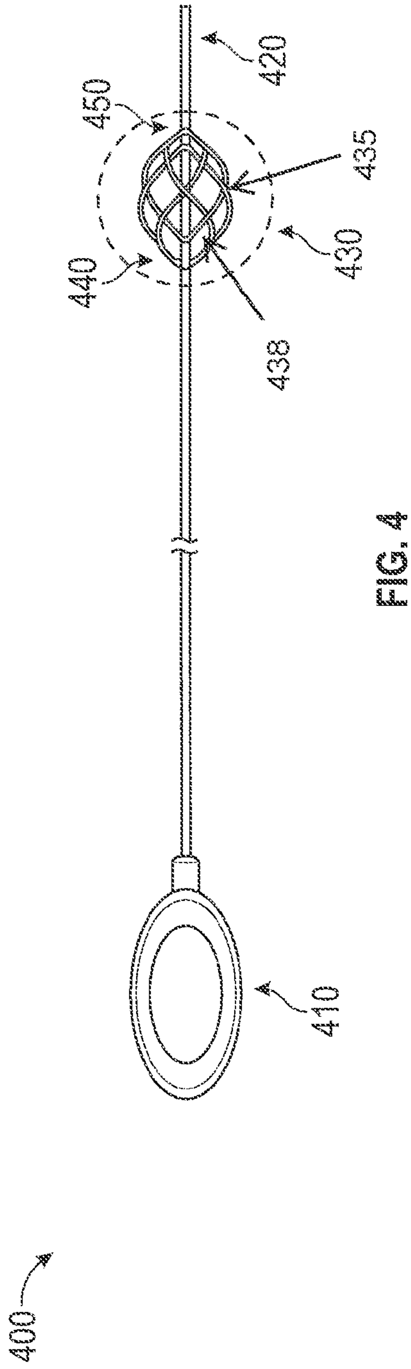
FIG. 4 illustrates a side view of the retriever catheter of FIG. 1.

With reference to the illustrated embodiments, FIG. 4 illustrates the retriever catheter 400 referred to in FIG. 1 but shown here in isolation. The retriever catheter 400 can be inserted through the ultrasound catheter 300 in the catheter system 100. For example, in the illustrated embodiment, the retriever catheter 400 can be inserted through a lumen extending through the ultrasound catheter for example the extrusion 330 or central lumen (shown with reference to FIG. 3) which can extend through the catheter and through the ultrasound element 370. In certain embodiments, the lumen through the which the retriever catheter 400 extends non-centrally through the ultrasound catheter, for example, along the side of the ultrasound element 370. In some examples, the retriever catheter can be positioned adjacent along a side of the ultrasound catheter 300. In some examples, the retriever catheter 400 can be inserted through the aspiration catheter 200 alongside the ultrasound catheter 370 or after the ultrasound catheter 300 has been removed. The retriever catheter 400 can include a handle 410 and a stylet 420 that connects to a retriever 430 located at the distal end of the retriever catheter 400. In some examples, the handle 410 can facilitate an action stop to prevent the stylet 420 from advancing too far into the retriever catheter. For example, the handle 410 can facilitate a push, pull, twist, etc. action. The retriever 430 can be bonded or welded to the stylet at a first end 440 of the retriever and may have a free end at a second end 450 of the retriever. The second end 450 can be a free end to allow the retriever to slide along the stylet 420. The retriever 430 can passively self-expand to retrieve a thrombus from the treatment site within the patient. In some examples, the retriever 430 may include a spiral basket 435 that may include at least one spline 438 (e.g., having six spiral splines, having two spiral splines, etc.). In some examples, the basket may contain nitinol. In some examples, the stylet 420 may be a guidewire. In some examples the guidewire may have a diameter of approximately 0.02 in. to approximately 0.04 in. The retriever 430 can be formed of a variety of materials such as, for example, nickel titanium (also known as nitinol).

In some examples, the catheter system may be used to remove a thrombus from the treatment site of the patient. The treatment site can be treated with ultrasound energy by use of the ultrasound catheter 300. In some examples, the treatment site may further be treated with an agent (e.g., a therapeutic compound). The agent may include microbubbles and/or phase changing nanodroplets that may assist in lysing the thrombus. The agent may be delivered to the treatment site by use of the ultrasound catheter and/or a separate catheter or device in certain combinations. A user can rotate the knob located on the ultrasound catheter, as described above, to direct the ultrasound energy (for example, at the frequencies described above) at various portion of the thrombus. This may soften or loosen the thrombus. In some aspects, the ultrasound catheter may delivery ultrasound energy at a power range of approximately 1 mW-25 W. In some aspects, the ultrasound transducer element can operate at a frequency of approximately 440 kHz-25 MHz and in certain embodiments the frequency can be in the range of 450 kHz-850 kHz and in certain aspects 650 kHz. The user can advance the ultrasound catheter through the length of the thrombus and continue to treat the thrombus with ultrasound energy as it is advanced. This can help to ensure the thrombus is effectively treated by delivering ultrasound energy to approximately the entire length of the thrombus. In some examples, the user can then insert the retriever catheter 400 and use the retriever to retrieve the thrombus and/or debris from the treatment site. In some examples, the retriever catheter 400 can be inserted through the aspiration catheter 200. At the same or similar time, the user can use the aspiration catheter 200 to aspirate the clot/thrombus, or any element of the clot/thrombus, into the aspiration catheter. This may help to more effectively remove the thrombus and/or debris from the treatment site. This may also help to ensure any fragment of the clot/thrombus and/or debris captured by the retriever remains in the retriever as the retriever is removed from the treatment site. In some examples, the ultrasound catheter may remain at the treatment site within the patient. In some examples, the ultrasound catheter can automatically rotate.

Figure 5:
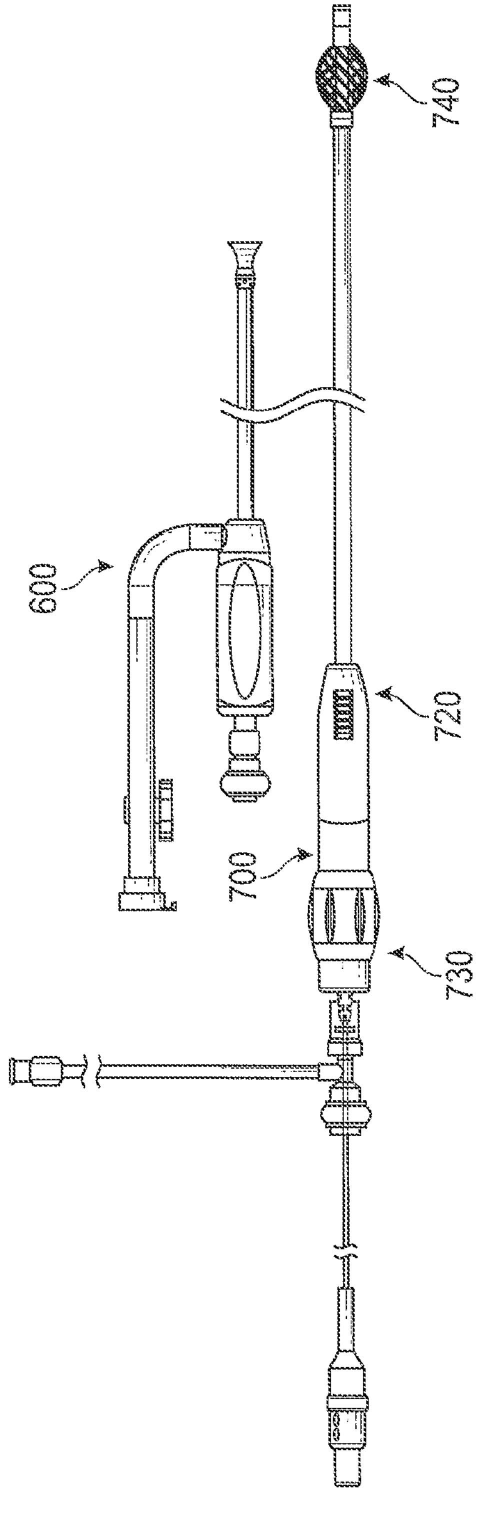
FIG. 5 illustrates another example embodiment of a catheter system that includes an aspiration catheter and a retriever catheter in combination with an ultrasound catheter.

With reference to the illustrated embodiments, FIG. 5 illustrates another embodiment of catheter system 500 that includes an aspiration catheter 600 and embodiment of an ultrasound catheter in combination with a retriever catheter 700. The catheter system 500 can be used to deliver ultrasound energy to a treatment site within a patient to assist in dissolving or lysing a thrombus located at the treatment site similar to the embodiment described above. The catheter system 500 can also be used to aspirate the thrombus at the treatment site. Additionally or alternatively, the catheter system 500 can be used to mechanically retrieve the thrombus from the treatment site. The catheter system 500 can also include at least one valve 610 that may be used to connect the various elements of the catheter system 500. In some examples, the valve 610 can include a hemostasis valve, which can minimize fluid loss during use of the catheter system 500. In some examples, the hemostasis valve 610 includes side port tubing. The catheter system 500 may further include an aspiration catheter with a flared end 620 which can be configured similar as the aspiration catheter and funnel described above. In some examples, the flared end can aspirate a greater area of the thrombus at once. In some examples, the ultrasound catheter in combination with the retriever catheter 700 can include an ultrasound element/ultrasound radiating element as described in the embodiments described above that may deliver ultrasound energy to a treatment site within a patient. In some examples, the ultrasound catheter in combination with the retriever catheter 700 can include a dial 720, which can control the deflection or movement of a distal tip of the ultrasound catheter in combination with the retriever catheter 700 through, for example, a pull wire as described in the embodiment described above. This may allow the catheter system 500 to more accurately direct or control where ultrasound energy is delivered. The ultrasound catheter in combination with the retriever catheter 700 can include a knob 730 that may be used to control the expansion or collapsing of a retriever 740 located at a distal end of the ultrasound catheter in combination with the retriever catheter 700.

Figure 6:
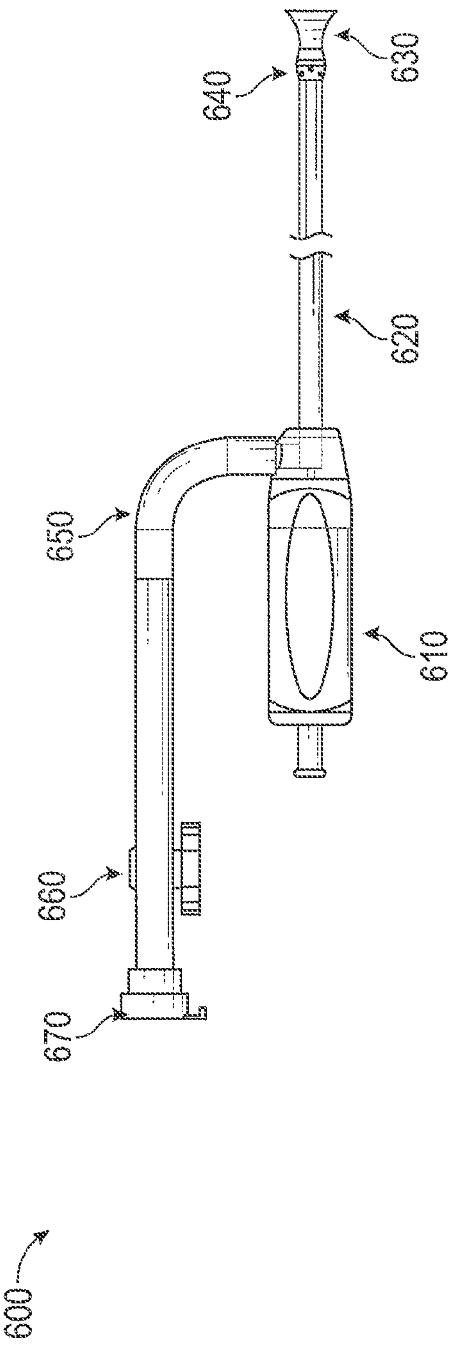
FIG. 6 illustrates an enlarged side view of the aspiration catheter of FIG. 5.

With reference to the illustrated embodiments, FIG. 6 illustrates the aspiration catheter 600. In some examples, the aspiration catheter 600 can be similar to the aspiration catheter described above with reference to FIG. 2 and FIG. 2A. As shown, the aspiration catheter 600 includes a handle 610, an extrusion 620, and a flared end 630. The extrusion 620 can extend through the handle 610 and connect to a distal interface 640 of the aspiration catheter. The distal interface 640 can be molded and bonded to the extrusion 620 and the flared end 630. In some examples, the distal interface 640 can be radiopaque. The flared end 630 can be bonded to the distal interface 640. In some examples, the flared end 630 can function as a lead-in feature of the aspiration catheter 600. In some examples, the flared end 630 can be collapsible and expand to the treatment site of the patient. For example, the flared end 630 can expand to a vessel wall of the treatment site of the patient. In some examples, the flared end 630 can direct aspiration of the aspiration catheter. For example, the flared end 630 can be open or closed to direct the aspiration. In some examples, the flared end 630 can be actively deployable. In some examples, the flared end 630 may include radiopaque features. In some examples, the flared end 630 may include nitinol. In some examples, the flared end 630 may have finger-like structures that may be connected by film, and may or may not be perforated. In some examples, the flared end 630 may be actuated by use of an outer cover or tube that may slide over or cover and cause the finger-like structures to draw closer together until the structures are in an isodiametric arrangement. The aspiration catheter can also include tubing 650, a one-way stop cock 660, and a vacuum syringe port 670 to assist in aspiration. In some examples, the tubing 650 can include flexible, large bore tubing. In some examples, the aspiration catheter can be articulated as explained with reference to FIG. 2A.

Figure 7:
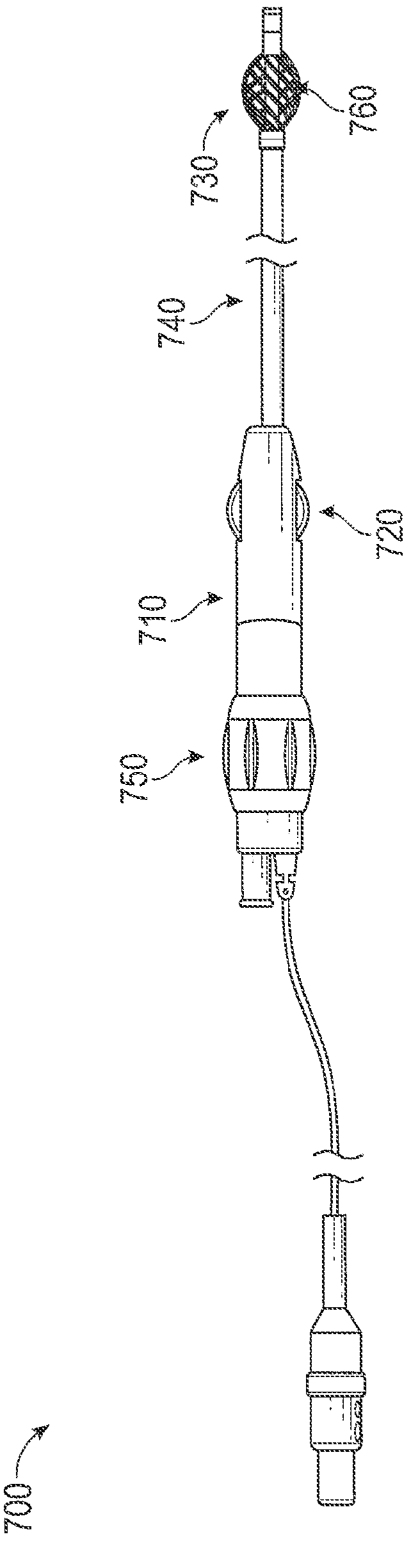
FIG. 7 illustrates a side view of the retriever catheter in combination with an ultrasound catheter of FIG. 5.

With reference to the illustrated embodiments, FIG. 7 illustrates an ultrasound catheter in combination with a retriever catheter 700. In some examples, the ultrasound catheter element 710 of ultrasound catheter in combination with a retriever catheter 700 can be similar to the ultrasound catheter described above. The ultrasound catheter element 710 can include an ultrasound element that may deliver ultrasound energy to the treatment site within the patient. As shown, the ultrasound catheter element 710 can include a dial 720. In some examples, the dial 720 may be a level, knob, slider, etc. The dial 720 may articulate a distal tip 730 of the ultrasound catheter element 710. The articulation of the distal tip 730 may direct where at the treatment site the ultrasound energy is delivered. The articulation of the distal end 730 can better direct the delivery of the ultrasound energy to the treatment site within the patient. For example, articulation of the distal end 730 can help to better dislodge the thrombus from the treatment site by better targeting a portion of the thrombus that may require additional treatment to dislodge or fragment. Additionally, articulation of the distal end 730 can better target the thrombus located in the treatment site as well. In some examples, an extrusion 740 of the ultrasound catheter element 710 can include pull wires that can allow + or −180-degree articulation of the distal tip 730. As shown, the retriever catheter element can include a knob 750 that may be located on the ultrasound catheter element 710. The knob 750 can be rotated to expand or collapse a retriever 760 located at the distal end of the ultrasound catheter in combination with a retriever catheter 700. As explained above, the retriever 760 can be used to retrieve a thrombus from the treatment site within the patient.

Figure 8:
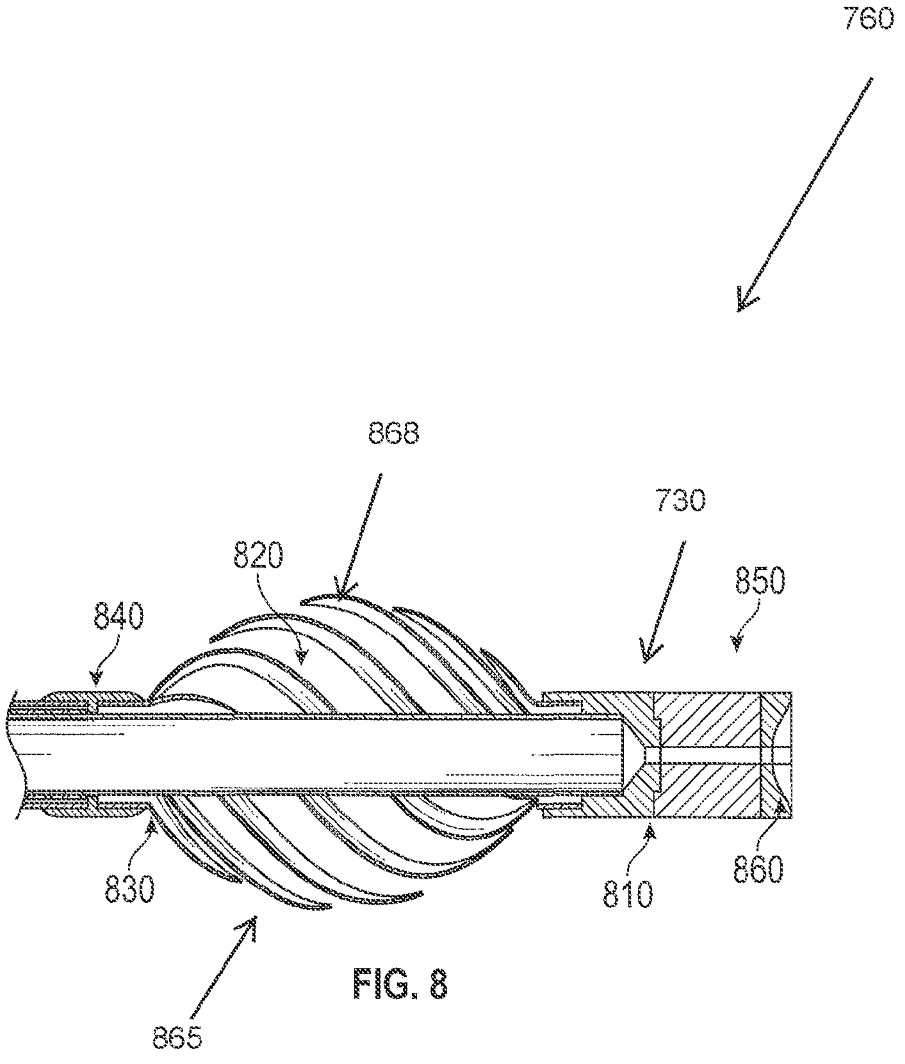
FIG. 8 illustrates an enlarged side view of another embodiment of a retriever in combination with an ultrasound catheter that can be used with a catheter system.

FIG. 8 illustrates a zoomed in view of the retriever 760 as referred to in FIG. 7. As shown, a distal end 810 of the retriever 760 may be connected to the distal tip 730 of the ultrasound catheter element. The distal end 810 can be molded and bonded to an inner extrusion 820 of the ultrasound catheter element. A proximal end 830 of the retriever 760 may be molded and bonded to an outer extrusion 840 of the ultrasound catheter element. In some examples the retriever and the outer extrusion can have radiopaque features and/or irrigation ports. As described above, the distal tip 730 can include an ultrasound element 850. In some examples, the ultrasound element 850 can be hollow, cylindrical, and include radiopaque features and/or irrigation ports. In some examples, the distal tip 730 can further include a concave lens 860. In certain aspects, the concave lens may be made of polycarbonate, ABS, PP, polysulfone, mylar, polystyrene, Epotek 301, epoxy doped with alumina, syntactic foam, HDPE, glass, Perspex, paralene, or other materials of the like. In some aspects, the material of the concave lens may have a phase velocity greater than blood. This can allow the ultrasound energy to be focused towards a front of the ultrasound radiating element. In certain embodiments, the concave lens 860 may assist in focusing the field to assist in treatment or removal lor the thrombus at the treatment site. In some examples, the retriever 760 may include a nitinol basket 865 and a plurality of splines 868. In some examples, the retriever 760 can include multiple heat set splines 868. In some examples, the retriever 760 may be actively expanded by rotation of the knob 750. For example, the knob 750 may be in a rack and pinion gearset configuration. For example, although not illustrated, the retriever catheter may include an inner catheter shaft that includes a perpendicular protruding shaft, which can form a T-shape with the inner catheter. The knob 750 can be molded to have, on the inner portion, material removed in the pattern of threads (i.e., threads of a nut). The inner shaft can be placed within the knob 750 where the protruding perpendicular shaft inserts into the threads. As the knob 750 is rotated, it can cause linear movement of the inner shaft for expansion or collapsing of the retriever 760. In other embodiments, the retriever can be a self-expanding element that is retained within a sheath that when positioned over the retriever constrains the retriever and when removed from the retriever causes the retriever to expand.

In some examples, the catheter system may be used to remove a clot/thrombus from the treatment site of the patient. the treatment site can be treated with ultrasound energy by use of the ultrasound catheter element of the ultrasound catheter in combination with the retriever catheter. The user can articulate the ultrasound catheter element of the ultrasound catheter in combination with the retriever catheter to direct the delivery of ultrasound energy at the treatment site. In some examples, the treatment site may further be treated with an agent. The agent may include microbubbles or phase changing nanodroplets that can assist in lysing the thrombus. A user can rotate the knob located on the ultrasound catheter, as described above, to direct the ultrasound energy at various portion of the thrombus. This may soften or loosen the thrombus. In some examples, the user can then control the retriever catheter of the ultrasound catheter in combination with the retriever catheter to expand or collapse the retriever. The expansion or collapsing of the retriever can help to retrieve the thrombus from the treatment site. At the same or similar time, the user can use the aspiration catheter to aspirate the thrombus into the aspiration catheter. In some examples, the ultrasound catheter in combination with the retriever catheter may remain at the treatment site within the patient.

Figure 9A:
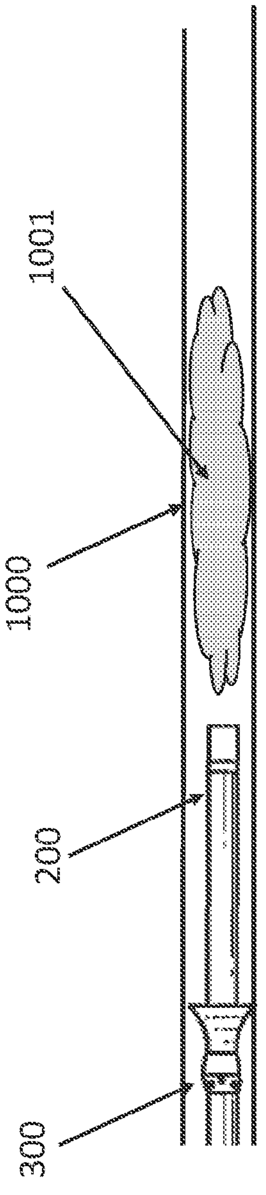
FIG. 9A schematically illustrates an embodiment of a catheter system that includes an aspiration catheter and an ultrasound catheter being advanced to a treatment site.
Figure 9B:
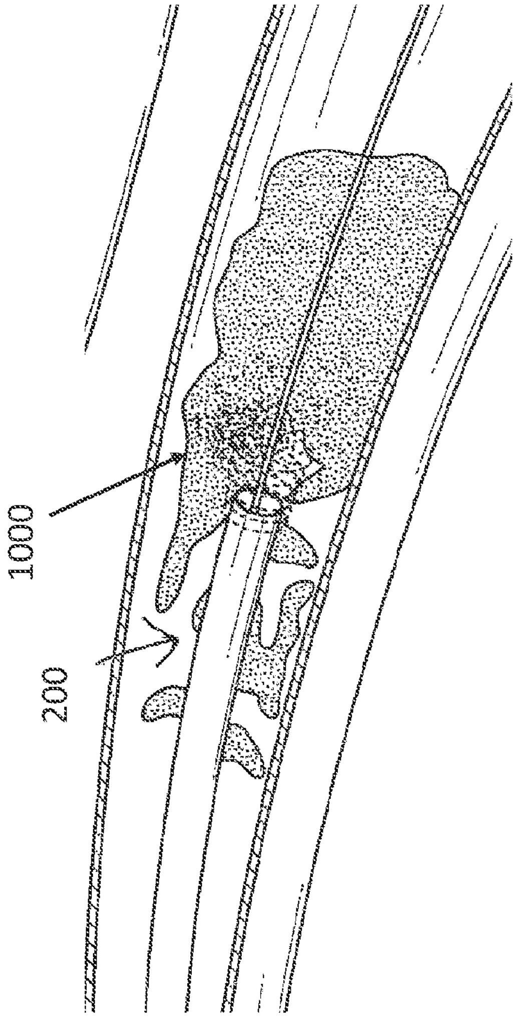
FIG. 9B schematically illustrates an embodiment of an ultrasound catheter being advanced through a clot at a treatment site.
Figure 9C:
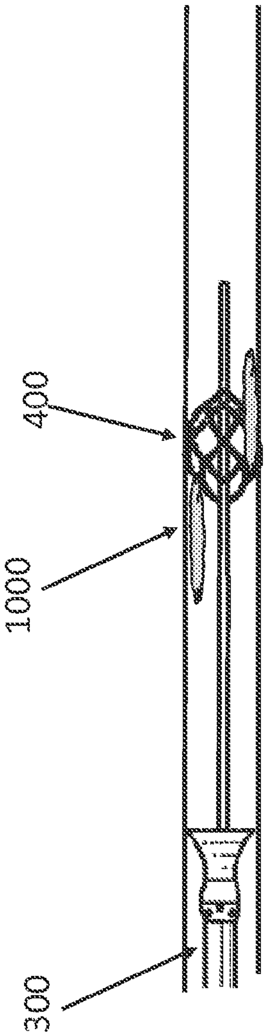
FIG. 9C schematically illustrates an embodiment of an aspiration catheter and a retriever catheter at a treatment site.

With reference to FIGS. 9A, 9B, and 9C, in some aspects, an aspiration catheter 300 (which can be according to aspects and embodiments described herein) may be introduced into a patient's vascular system through an access site and then advanced to the treatment site 1000. In some aspects, the aspiration catheter 300 may be advanced to an area near the treatment site. In some aspects, the aspiration catheter may be advanced to an area between an insertion site and the treatment site. After introduction of the aspiration catheter 300, an ultrasound catheter 200 (which can be according to aspects and embodiments described herein) may be introduced through the aspiration catheter 300 and advanced to the treatmensite. In certain embodiments, the ultrasound catheter can be advanced over a guidewire. The ultrasound catheter 200, in the illustrated embodiment, may be advanced through the aspiration catheter 300 to then be introduced to the treatment site 1000 which includes a clot 1001 (e.g., a thrombus). The ultrasound catheter 200 may be used to deliver ultrasound (through the ultrasound element), and/or deliver microbubbles and/or metastable phase change nanodroplets and rtPA or other therapeutic compounds as described herein (e.g., a lytic) to the treatment site as described above, for example, through the lumen 201 of the ultrasound catheter or through other passages in the catheter system or ultrasound catheter. This can allow for treatment of the thrombus located at the treatment site. For example, delivering microbubbles and/or metastable phase change nanodroplets can create microchannels within the thrombus. The ultrasound catheter can deliver ultrasound energy or ultrasound treatment to the thrombus. In certain aspects, the ultrasound catheter may deliver ultrasound energy at a power range of approximately 1 mW-25 W. In certain aspects, the ultrasound transducer element can operate at a frequency of approximately 440 kHz-25 MHz and in certain embodiments the frequency can be in the range of 450 kHz-850 kHz and in certain aspects 650 kHz. The ultrasound and therapeutic compound can be delivered simultaneously and/or not simultaneously. The ultrasound catheter 200 can continue to deliver treatment to the thrombus as it is advanced through the length of the thrombus (see FIG. 9B). For example, in certain aspects, the ultrasound catheter is first positioned near the thrombus or within the beginning of the thrombus and then after treatment with ultrasound and a therapeutic compound begins, the ultrasound catheter can be advanced into (or further into) the thrombus. Advantageously, the microbubbles and/or metastable phase change nanodroplets and rtPA or other therapeutic compounds (e.g., a lytic) in combination with the ultrasound may aid in boring a hole or passage through the clot. The ultrasound and microbubbles and/or metastable phase change nanodroplets and rtPA or other therapeutic compounds (e.g., a lytic) can be delivered together or sequentially with each other. In certain aspects, after an initial treatment period with the ultrasound and/or therapeutic compound wherein the distal end of the ultrasound catheter is positioned at, near, or with the beginning of a clot/obstruction, the ultrasound catheter can be advanced 25% through length of thrombus, 50% through length of thrombus, 100% through length of thrombus and then further treatment with ultrasound and/or therapeutic compound can be conducted such that the length of the thrombus can be treated. The ultrasound catheter can then be removed from the treatment site. As noted above, some examples, a distal end of the ultrasound catheter 200 may be configured to articulate. This may allow a targeted ultrasound treatment to be delivered to the treatment site particularly as the ultrasound catheter is advanced through a length of thrombus. Articulation of the distal end of the ultrasound catheter may allow for the thrombus to be treated from different angles and/or may allow for a greater area of the treatment site to be treated more effectively. This articulation and targeted ultrasound treatment can occur as the ultrasound catheter at the beginning of treatment (e.g., at the front of the clot or obstruction) and/or as the ultrasound catheter is advanced through the clot (and/or withdrawn or moved through the treatment site after an initial treatment period). For example, after imaging (e.g., by fluoroscopy or other imaging techniques) and identifying residual clot, the distal end of the ultrasound catheter can be articulated between + or −180 degrees from a longitudinal axis of the catheter and in certain aspects between + or −90 degrees longitudinal axis of the catheter and in certain aspects between + or −45 degrees longitudinal axis of the catheter to direct ultrasound energy to the identified residual clot. This targeted treatment can be conducted as the ultrasound catheter is advanced through the clot and/or before initially advancing the ultrasound catheter through the clot and/or after a segment of clot/obstruction has been treated and the ultrasound catheter is being removed. An advantage of targeted ultrasound and movement through the clot can be the enhanced mechanical assistance/action in engaging thrombus for better/improved treatment which may allow new regions for treatment, more microchannels, and/or greater binding sites for lytic leading to improved performance and outcomes. With reference to FIG. 9C, a retriever catheter 400 (according to aspects described herein) may then be introduced to the treatment site. The retriever catheter 400 can be advanced through the aspiration catheter to be introduced to the treatment site 100. The retriever catheter may be advanced to the most outer end of the treatment (e.g., entirely or substantially through the clot) site and deploy a retriever. The retriever may capture the degraded and/or residual thrombus at the treatment site. The retriever catheter may then retract the retriever from the treatment site and into the aspiration catheter. In certain aspects, aspiration is applied through the aspiration catheter as the retriever is withdrawn into the aspiration catheter. The aspiration catheter may then aspirate the treatment site to direct the degraded and/or residual thrombus into the aspiration catheter. The advancement of the retriever catheter, deployment of the retriever, retraction of retriever, and aspiration of the treatment site may be repeat until the treatment site is free or mostly free of thrombus. In certain embodiments, aspiration may not be applied as the retriever is withdrawn into the aspiration catheter and, in certain embodiments, aspiration may not be applied as the retriever captures the thrombus during treatment. As noted above, in certain aspects, the retriever catheter can be advanced through the ultrasound catheter or alongside the ultrasound catheter through the aspiration catheter. In certain aspects, the retriever can be formed on a portion of the ultrasound catheter as described above.

Combinations

The foregoing description and examples are set forth merely to illustrate the inventive concepts and are not intended as being limiting. Each of the disclosed aspects and examples of the present disclosure may be considered individually or in combination with other aspects, examples, and variations of the disclosure. In addition, unless otherwise specified, none of the steps of the methods of the present disclosure are confined to any particular order of performance. Reasonable modifications of the disclosed examples incorporating the spirit and substance of the disclosure are within the scope of the present disclosure. Furthermore, all references cited herein are incorporated by reference in their entirety. Headings used herein are for organizational purposes only and should not be used to unduly limit claim scope or embodiments.

While the methods and devices described herein may be susceptible to various modifications and alternative forms, specific examples thereof have been shown in the drawings and are herein described in detail. It should be understood, however, that the embodiments are not to be limited to the particular devices or methods disclosed, but, to the contrary, cover all reasonable modifications, equivalents, and alternatives falling within the spirit and scope of the various examples described and the appended claims. Further, the disclosure herein of any particular feature, aspect, method, property, characteristic, quality, attribute, element, or the like in connection with an example can be used in all other examples set forth herein. Any methods disclosed herein need not be performed in the order recited. Depending on the example, one or more acts, events, or functions of any of the algorithms, methods, or processes described herein can be performed in a different sequence, can be added, merged, or left out altogether (e.g., not all described acts or events are necessary for the practice of the algorithm). Algorithms, modules, blocks, steps, boxes, elements, features, etc. may be stored in machine-readable memory. In some examples, acts or events can be performed concurrently, e.g., through multi-threaded processing, interrupt processing, or multiple processors or processor cores or on other parallel architectures, rather than sequentially. Further, no element, feature, block, box, or step, or group of elements, features, blocks, boxes, or steps, are necessary or indispensable to each example. Additionally, all possible combinations, subcombinations, and rearrangements of systems, methods, features, elements, modules, blocks, boxes, and so forth are within the scope of this disclosure. The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed. Thus, some examples may be performed using the sequence of operations described herein, while other examples may be performed following a different sequence of operations.

The various illustrative logical blocks, boxes, modules, processes, methods, and algorithms described in connection with the examples disclosed herein can be implemented as electronic hardware, computer software, or combinations of both. To clearly illustrate this interchangeability of hardware and software, various illustrative components, blocks, modules, operations, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the examples disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The blocks, operations, or steps of a method, process, or algorithm described in connection with the examples disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, an optical disc (e.g., CD-ROM or DVD), or any other form of volatile or non-volatile computer-readable storage medium known in the art. A storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that some examples include, while other examples do not include, certain features, elements, and/or states. Thus, such conditional language is not generally intended to imply that features, elements, blocks, and/or states are in any way required for one or more examples or that one or more examples necessarily include logic for deciding, with or without author input or prompting, whether these features, elements and/or states are included or are to be performed in any particular example.

The methods disclosed herein may include certain actions taken by a practitioner; however, the methods can also include any third-party instruction of those actions, either expressly or by implication. For example, actions such as "advancing a catheter" include "instructing advancing a catheter."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 mm" includes "1 mm." Phrases preceded by a term such as "substantially" include the recited phrase and should be interpreted based on the circumstances (e.g., as much as reasonably possible under the circumstances). For example, "substantially parallel" includes "parallel." Unless stated otherwise, all measurements are at standard conditions including temperature and pressure. The phrase "at least one of" is intended to require at least one item from the subsequent listing, not one type of each item in the subsequent listing. For example, "at least one of A, B, and C" can include A, B, C, A and B, A and C, B and C, or A, B, and C.

Unless otherwise defined, all technical terms used herein have the same meaning as commonly understood by one of ordinary skill in the art to which the present disclosure pertains. As used herein, the singular forms "a," "an," and "the" can also include the plural forms, unless the context clearly indicates otherwise. As used herein, the terms "comprises" and/or "comprising," can specify the presence of stated features, steps, operations, elements, components, and/or groups, but do not preclude the presence or addition of one or more other features, steps, operations, elements, components, and/or groups. As used herein, the term "and/or" can include any and all combinations of one or more of the associated listed items. As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or FIGURES unless specifically indicated otherwise.

What is claimed is:

1. A method for treating a patient with a thromboembolism, the method comprising:

positioning an ultrasound catheter in a first position, wherein in the first position:

a distal end of the ultrasound catheter is positioned proximal to a treatment site having a clot in a vessel, and a delivery component of the ultrasound catheter faces the treatment site;

delivering, with the ultrasound catheter in the first position, targeted ultrasound energy from the delivery component to the treatment site for an initial treatment period;

after the initial treatment period, advancing the ultrasound catheter to a second position in which the distal end of the ultrasound catheter is positioned in the treatment site;

articulating, with the ultrasound catheter in the second position, the distal end of the ultrasound catheter such that the delivery component of the ultrasound catheter faces a residual clot, wherein articulating the distal end of the ultrasound catheter comprises deflecting the distal end of the ultrasound catheter; and delivering, after articulating the distal end of the ultrasound catheter, targeted ultrasound energy from the delivery component to the residual clot.

2. The method of claim 1, further comprising advancing an introducer sheath into a patient's vascular system before advancing the ultrasound catheter, and advancing the ultrasound catheter through the introducer sheath and into the treatment site.

3. The method of claim 2, wherein the introducer sheath comprises an aspiration catheter.

4. The method of claim 3, wherein the aspiration catheter includes an expandable funnel at a distal end of the aspiration catheter.

5. The method of claim 1, further comprising delivering a therapeutic compound from the ultrasound catheter to the treatment site.

6. The method of claim 5, further comprising delivering the therapeutic compound through a lumen of the ultrasound catheter, and wherein the therapeutic compound comprises at least one of a lytic, microbubbles or nanodroplets.

7. The method of claim 1, wherein the delivery component comprises an ultrasound element at the distal end of the ultrasound catheter.

8. The method of claim 1, further comprising rotating the ultrasound catheter.

9. The method of claim 1, wherein articulating the distal end of the ultrasound catheter comprises articulating the distal end of the ultrasound catheter to an angle greater than −180 degrees and less than 180 degrees with respect to a longitudinal axis of the ultrasound catheter.

10. The method of claim 1, wherein articulating the distal end of the ultrasound catheter comprises articulating the distal end of the ultrasound catheter such that the delivery component of the ultrasound catheter faces the residual clot and a wall of the vessel.

11. A method for treating a patient with a thromboembolism, the method comprising:

positioning an ultrasound catheter in a first position, wherein, in the first position, a delivery component of the ultrasound catheter faces a clot in a vessel;

delivering, with the ultrasound catheter in the first position, targeted ultrasound energy from the delivery component and a therapeutic compound from a lumen of the ultrasound catheter to the clot for an initial treatment period;

after the initial treatment period, positioning the ultrasound catheter in a second position;

articulating, with the ultrasound catheter in the second position, a distal end of the ultrasound catheter with respect to a longitudinal axis of the ultrasound catheter, wherein articulating the distal end of the ultrasound catheter comprises deflecting the distal end of the ultrasound catheter; and delivering, after articulating the distal end of the ultrasound catheter, targeted ultrasound energy from the delivery component and the therapeutic compound from the lumen of the ultrasound catheter to a residual clot.

12. The method of claim 11, further comprising advancing an introducer sheath into a patient's vascular system before advancing the ultrasound catheter, and advancing the ultrasound catheter through the introducer sheath and into the vessel.

13. The method of claim 12, wherein the introducer sheath comprises an aspiration catheter.

14. The method of claim 13, wherein the aspiration catheter includes an expandable funnel at a distal end of the aspiration catheter.

15. The method of claim 11, wherein the delivery component is positioned on the distal end of the ultrasound catheter.

16. The method of claim 11, wherein the therapeutic compound comprises at least one of a lytic, microbubbles or nanodroplets.

17. The method of claim 11, wherein the delivery component comprises an ultrasound element.

18. The method of claim 11, further comprising rotating the ultrasound catheter.

19. The method of claim 11, wherein articulating the distal end of the ultrasound catheter comprises articulating the distal end of the ultrasound catheter to an angle greater than −180 degrees and less than 180 degrees with respect to a longitudinal axis of the ultrasound catheter.

20. The method of claim 11, wherein articulating the distal end of the ultrasound catheter comprises articulating the distal end of the ultrasound catheter such that the delivery component of the ultrasound catheter faces the residual clot and a wall of the vessel.

* * * * *